(12) United States Patent
Bagaoisan et al.

(10) Patent No.: US 9,289,195 B2
(45) Date of Patent: Mar. 22, 2016

(54) AUTO-RETRACTION APPARATUS AND METHODS FOR SEALING A VASCULAR PUNCTURE

(75) Inventors: Celso J. Bagaoisan, Union City, CA (US); Nicanor Domingo, Brisbane, CA (US); Farhad Khosravi, Los Altos Hills, CA (US); Suresh S. Pai, Mountain View, CA (US)

(73) Assignee: Access Closure, Inc., Santa Clara, CA (US)

( * ) Notice: Subject to any disclaimer, the term of this patent is extended or adjusted under 35 U.S.C. 154(b) by 2605 days.

(21) Appl. No.: 10/806,952

(22) Filed: Mar. 22, 2004

(65) Prior Publication Data
US 2004/0267308 A1 Dec. 30, 2004

Related U.S. Application Data

(63) Continuation-in-part of application No. 10/454,362, filed on Jun. 4, 2003, now Pat. No. 7,331,979.

(51) Int. Cl.
*A61B 17/08* (2006.01)
*A61B 17/00* (2006.01)
(Continued)

(52) U.S. Cl.
CPC ..... *A61B 17/0057* (2013.01); *A61B 2017/0065* (2013.01); *A61B 2017/00495* (2013.01);
(Continued)

(58) Field of Classification Search
CPC ................... A61B 17/0057; A61B 17/00491; A61B 2017/0065
USPC ........................... 606/213, 232; 128/887, 898
See application file for complete search history.

(56) References Cited

U.S. PATENT DOCUMENTS

| 2,115,492 A | 4/1938 | Kober |
| 2,365,039 A | 12/1944 | Andresen |

(Continued)

FOREIGN PATENT DOCUMENTS

| EP | 0 476 178 A1 | 3/1992 |
| EP | 0 482 350 B1 | 4/1992 |

(Continued)

OTHER PUBLICATIONS

Partial PCT International Search Report for PCT/US2005/007990, Applicant AccessClosure, Forms PCT/ISA/206, dated Oct. 24, 2005, (6 pages).

(Continued)

*Primary Examiner* — Diane Yabut
(74) *Attorney, Agent, or Firm* — Nada J. Ardeleanu

(57) ABSTRACT

Apparatus for sealing a puncture communicating with a blood vessel includes an introducer sheath, an occlusion member with a balloon thereon, a retraction assembly, and a syringe assembly including sealing material therein. During use, the introducer sheath is introduced into the puncture. With the balloon in a collapsed state, the occlusion member is introduced through the introducer sheath until the balloon is disposed within the vessel. The introducer sheath is coupled to the retraction assembly, the balloon is expanded, and the occlusion member is partially withdrawn to seal the puncture. A sealing compound is delivered from the syringe assembly through the introducer sheath into the puncture, the syringe assembly triggering the retraction assembly, whereupon the introducer sheath is automatically withdrawn at least partially from the puncture, delivering the sealing compound along the puncture.

18 Claims, 26 Drawing Sheets

(51) Int. Cl.
*A61M 25/10* (2013.01)
*A61M 25/06* (2006.01)

(52) U.S. Cl.
CPC ............... *A61B2017/00557* (2013.01); *A61B 2017/00637* (2013.01); *A61B 2017/00986* (2013.01); *A61M 25/1002* (2013.01); *A61M 25/1018* (2013.01); *A61M 2025/0681* (2013.01)

(56) References Cited

U.S. PATENT DOCUMENTS

| | | | |
|---|---|---|---|
| 3,765,419 A | 10/1973 | Usher | |
| 4,002,173 A | 1/1977 | Manning et al. | |
| 4,260,077 A | 4/1981 | Schroeder | |
| 4,327,709 A | 5/1982 | Hanson et al. | |
| 4,362,150 A | 12/1982 | Lombardi, Jr. et al. | |
| 4,540,404 A | 9/1985 | Wolvek | |
| 4,598,707 A | 7/1986 | Agdanowski et al. | |
| 4,655,211 A | 4/1987 | Sakamoto et al. | |
| 4,664,857 A | 5/1987 | Nambu | |
| 4,734,097 A | 3/1988 | Tanabe et al. | |
| 4,738,658 A | 4/1988 | Magro et al. | |
| 4,801,434 A | 1/1989 | Kido et al. | |
| 4,838,280 A | 6/1989 | Haaga | |
| 4,838,864 A | 6/1989 | Peterson | |
| 4,852,568 A | 8/1989 | Kensey | |
| 4,890,612 A | 1/1990 | Kensey | |
| 4,948,092 A | 8/1990 | Kasper et al. | |
| 5,021,059 A | 6/1991 | Kensey et al. | |
| 5,061,274 A | 10/1991 | Kensey | |
| 5,085,249 A | 2/1992 | Dragan et al. | |
| 5,104,375 A | 4/1992 | Wolf et al. | |
| 5,104,389 A | 4/1992 | Deem et al. | |
| 5,108,421 A | 4/1992 | Fowler | |
| 5,192,300 A | 3/1993 | Fowler | |
| 5,192,302 A | 3/1993 | Kensey et al. | |
| 5,221,259 A | 6/1993 | Weldom et al. | |
| 5,222,974 A | 6/1993 | Kensey et al. | |
| 5,258,042 A | 11/1993 | Mehta | |
| 5,259,835 A | 11/1993 | Clark et al. | |
| 5,275,616 A | 1/1994 | Fowler | |
| 5,290,310 A | 3/1994 | Makower et al. | |
| 5,292,332 A | 3/1994 | Lee | |
| 5,306,254 A | 4/1994 | Nash et al. | |
| 5,320,639 A | 6/1994 | Rudnick | |
| 5,324,306 A | 6/1994 | Makower et al. | |
| 5,334,216 A | 8/1994 | Vidal | |
| 5,370,660 A | 12/1994 | Weinstein | |
| 5,383,896 A | 1/1995 | Gershony et al. | |
| RE34,866 E | 2/1995 | Kensey et al. | |
| 5,391,183 A | 2/1995 | Janzen et al. | |
| 5,409,703 A | 4/1995 | McAnalley et al. | |
| 5,413,571 A | 5/1995 | Katsaros et al. | |
| 5,419,765 A | 5/1995 | Weldon et al. | |
| 5,431,639 A * | 7/1995 | Shaw ........................ | 604/264 |
| 5,437,292 A | 8/1995 | Kipshidze et al. | |
| 5,437,631 A | 8/1995 | Janzen | |
| 5,441,517 A | 8/1995 | Kensey et al. | |
| 5,443,481 A | 8/1995 | Lee | |
| 5,464,396 A | 11/1995 | Barta et al. | |
| 5,486,195 A | 1/1996 | Myers et al. | |
| 5,489,278 A | 2/1996 | Abrahamson | |
| 5,514,158 A | 5/1996 | Kanesaka | |
| 5,529,577 A | 6/1996 | Hammerslag | |
| 5,550,187 A | 8/1996 | Rhee | |
| 5,571,181 A | 11/1996 | Li | |
| 5,580,923 A | 12/1996 | Yeung | |
| 5,584,815 A | 12/1996 | Pawelka et al. | |
| 5,591,204 A | 1/1997 | Janzen et al. | |
| 5,591,205 A | 1/1997 | Fowler | |
| 5,601,602 A | 2/1997 | Fowler | |
| 5,626,601 A * | 5/1997 | Gershony et al. .......... | 606/194 |
| 5,637,086 A | 6/1997 | Ferguson et al. | |
| 5,643,464 A | 7/1997 | Rhee | |
| 5,660,849 A | 8/1997 | Polson et al. | |
| 5,700,477 A | 12/1997 | Rosenthal et al. | |
| 5,716,375 A | 2/1998 | Fowler | |
| 5,718,916 A | 2/1998 | Scherr | |
| 5,725,498 A | 3/1998 | Janzen et al. | |
| 5,725,551 A | 3/1998 | Myers et al. | |
| 5,728,122 A | 3/1998 | Leschinsky et al. | |
| 5,731,368 A | 3/1998 | Stanley et al. | |
| 5,741,223 A | 4/1998 | Janzen et al. | |
| 5,744,153 A | 4/1998 | Yewey et al. | |
| 5,752,974 A | 5/1998 | Rhee et al. | |
| 5,780,044 A | 7/1998 | Yewey et al. | |
| 5,782,860 A | 7/1998 | Epstein et al. | |
| 5,785,679 A | 7/1998 | Abolfathi et al. | |
| 5,795,331 A | 8/1998 | Cragg et al. | |
| 5,814,016 A | 9/1998 | Valley et al. | |
| 5,830,130 A | 11/1998 | Janzen et al. | |
| 5,836,970 A | 11/1998 | Pandit | |
| 5,843,124 A | 12/1998 | Hammerslag | |
| 5,868,778 A | 2/1999 | Gershony et al. | |
| 5,916,236 A | 6/1999 | Muijs Van de Moer et al. | |
| 5,922,009 A | 7/1999 | Epstein et al. | |
| 5,928,266 A | 7/1999 | Kontos | |
| 5,941,847 A | 8/1999 | Huber et al. | |
| 5,948,429 A | 9/1999 | Bell et al. | |
| 5,948,829 A | 9/1999 | Wallajapet et al. | |
| 5,951,583 A | 9/1999 | Jensen et al. | |
| 5,951,589 A | 9/1999 | Epstein et al. | |
| 5,957,952 A | 9/1999 | Gershony | |
| 5,972,375 A | 10/1999 | Truter et al. | |
| 5,973,014 A | 10/1999 | Funk et al. | |
| 6,017,359 A | 1/2000 | Gershony et al. | |
| 6,022,361 A | 2/2000 | Epstein et al. | |
| 6,027,471 A | 2/2000 | Fallon et al. | |
| 6,045,570 A * | 4/2000 | Epstein et al. ............. | 606/214 |
| 6,048,358 A | 4/2000 | Barak | |
| 6,051,248 A | 4/2000 | Sawhney et al. | |
| 6,056,768 A | 5/2000 | Cates et al. | |
| 6,056,769 A | 5/2000 | Epstein et al. | |
| 6,063,061 A | 5/2000 | Wallace et al. | |
| 6,083,522 A | 7/2000 | Chu | |
| 6,090,130 A | 7/2000 | Nash et al. | |
| 6,117,145 A | 9/2000 | Wood et al. | |
| 6,152,943 A | 11/2000 | Sawhney | |
| 6,162,240 A * | 12/2000 | Cates et al. ................. | 606/213 |
| 6,162,241 A | 12/2000 | Coury et al. | |
| 6,165,201 A | 12/2000 | Sawhney | |
| 6,179,862 B1 | 1/2001 | Sawhney | |
| 6,223,936 B1 | 5/2001 | Jeanbourquin | |
| 6,238,412 B1 | 5/2001 | Dubrul | |
| 6,271,278 B1 | 8/2001 | Park et al. | |
| 6,287,323 B1 | 9/2001 | Hammerslag | |
| 6,296,658 B1 | 10/2001 | Gershony | |
| 6,299,597 B1 | 10/2001 | Buscemi et al. | |
| 6,302,898 B1 | 10/2001 | Edwards et al. | |
| 6,325,789 B1 | 12/2001 | Janzen et al. | |
| 6,350,274 B1 | 2/2002 | Li | |
| 6,368,300 B1 | 4/2002 | Fallon et al. | |
| 6,371,975 B2 | 4/2002 | Cruise et al. | |
| 6,379,373 B1 | 4/2002 | Sawhney | |
| 6,458,147 B1 | 10/2002 | Cruise et al. | |
| 6,464,712 B1 | 10/2002 | Epstein | |
| 6,475,177 B1 | 11/2002 | Suzuki | |
| 6,514,534 B1 | 2/2003 | Sawhney | |
| 6,562,059 B2 * | 5/2003 | Edwards et al. ............ | 606/213 |
| 6,566,406 B1 | 5/2003 | Pathak | |
| 6,569,185 B2 | 5/2003 | Ungs | |
| 6,605,294 B2 | 8/2003 | Sawhney | |
| 6,608,117 B1 | 8/2003 | Gvozdic | |
| 6,610,026 B2 | 8/2003 | Cragg | |
| 6,613,070 B2 | 9/2003 | Redmond et al. | |
| 6,626,861 B1 | 9/2003 | Hart | |
| 6,626,918 B1 | 9/2003 | Ginn | |
| 6,635,068 B1 | 10/2003 | Dubrul | |
| 6,689,148 B2 | 2/2004 | Sawhney | |
| 6,703,047 B2 | 3/2004 | Sawhney | |
| 6,774,151 B2 | 8/2004 | Malmgren et al. | |
| 6,808,524 B2 | 10/2004 | Lopath et al. | |
| 6,818,008 B1 | 11/2004 | Cates | |
| 6,818,018 B1 | 11/2004 | Sawhney | |

(56) References Cited

U.S. PATENT DOCUMENTS

| | | |
|---|---|---|
| 6,863,924 B2 | 3/2005 | Ranganathan et al. |
| 6,887,974 B2 | 5/2005 | Pathak |
| 6,960,617 B2 | 11/2005 | Omidian et al. |
| 6,994,686 B2 | 2/2006 | Cruise et al. |
| 7,189,229 B2 | 3/2007 | Lopath et al. |
| 7,335,220 B2 | 2/2008 | Khosravi |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney |
| 2002/0111392 A1 | 8/2002 | Cruise |
| 2002/0111651 A1 | 8/2002 | Ungs |
| 2002/0188319 A1 | 12/2002 | Morris et al. |
| 2002/0193808 A1* | 12/2002 | Belef et al. .................. 606/139 |
| 2003/0008831 A1 | 1/2003 | Yang et al. |
| 2003/0012734 A1 | 1/2003 | Pathak |
| 2003/0051735 A1 | 3/2003 | Pavcnik |
| 2003/0088269 A1 | 5/2003 | Ashby |
| 2003/0088271 A1 | 5/2003 | Cragg et al. |
| 2003/0135234 A1 | 7/2003 | Fisher et al. |
| 2003/0135235 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeldt |
| 2004/0098017 A1* | 5/2004 | Saab et al. .................. 606/192 |
| 2004/0122350 A1 | 6/2004 | Zhong |
| 2004/0236262 A1 | 11/2004 | McIntosh et al. |
| 2004/0249342 A1 | 12/2004 | Khosravi |
| 2004/0267308 A1 | 12/2004 | Bagaoisan |
| 2005/0085852 A1 | 4/2005 | Ditter |
| 2006/0034930 A1 | 2/2006 | Khosravi |
| 2006/0100664 A1 | 5/2006 | Pai |
| 2006/0253072 A1 | 11/2006 | Pai |

FOREIGN PATENT DOCUMENTS

| | | |
|---|---|---|
| JP | 2002513308 A | 5/2002 |
| WO | WO 92/22252 | 12/1992 |
| WO | 9533510 A1 | 12/1995 |
| WO | 0014155 A1 | 3/2000 |
| WO | WO 00/19912 | 4/2001 |
| WO | WO 03/094749 | 11/2003 |

OTHER PUBLICATIONS

PCT International Search Report for PCT/US2005/007990, Applicant—Accessclosure, Inc., Forms PCT/ISA/210, and 220, dated Jan. 4, 2006 (8 pages).

PCT Written Opinion of the International Search Authority for PCT/US2005/007990, Applicant:—Accessclosure, Inc., Form PCT/ISA/237, dated Jan. 4, 2006 (8 pages).

Office Action and Response for pending U.S. Appl. No. 11/112,971 dated Apr. 28, 2008 and Jul. 28, 2008, 31 pages.

International Search Report for Application No. PCT/US2006/014562, mailed on Dec. 8, 2006, 5 pages.

PCT International Search Report for PCT/US2004/016938, Applicant: AccessClossure, Inc., Forms PCT/ISA/210 and 220, dated Mar. 2, 2005,13 pages.

PCT International Search Report for PCT/US2006/014562, Applicant: AccessClossure, Inc., Forms PCT/ISA/210 and PCT/ISA/220, dated Aug. 12, 2006,13 pages.

PCT Partial International Search Report for PCT/US2004/016938, Applicant: AccessClossure, Inc., Forms PCT/ISA/206, dated Nov. 12, 2004,4 pages.

* cited by examiner

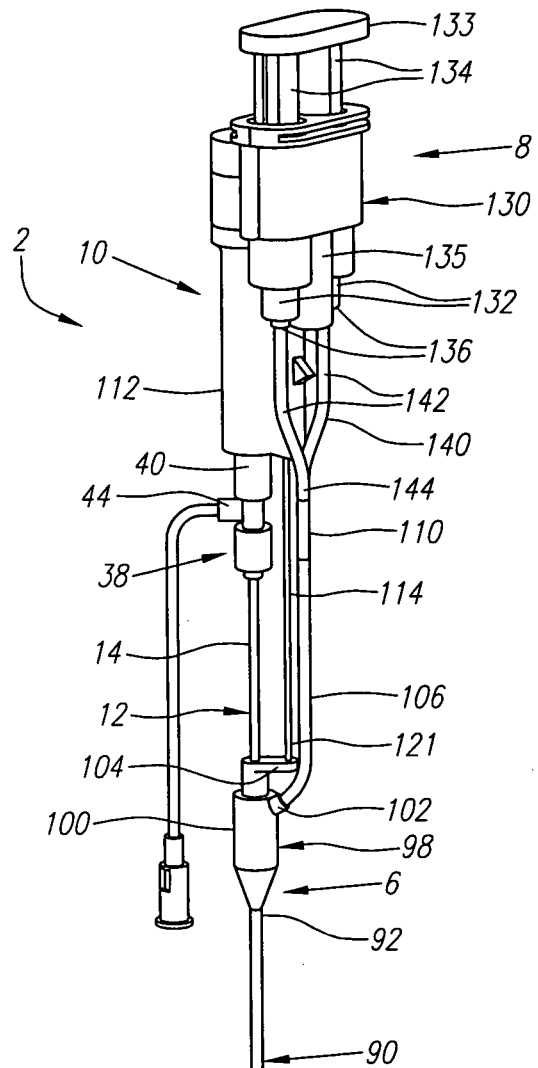
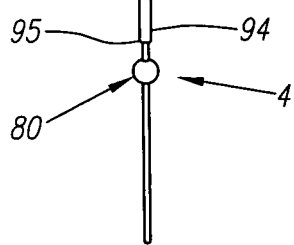
FIG. 1

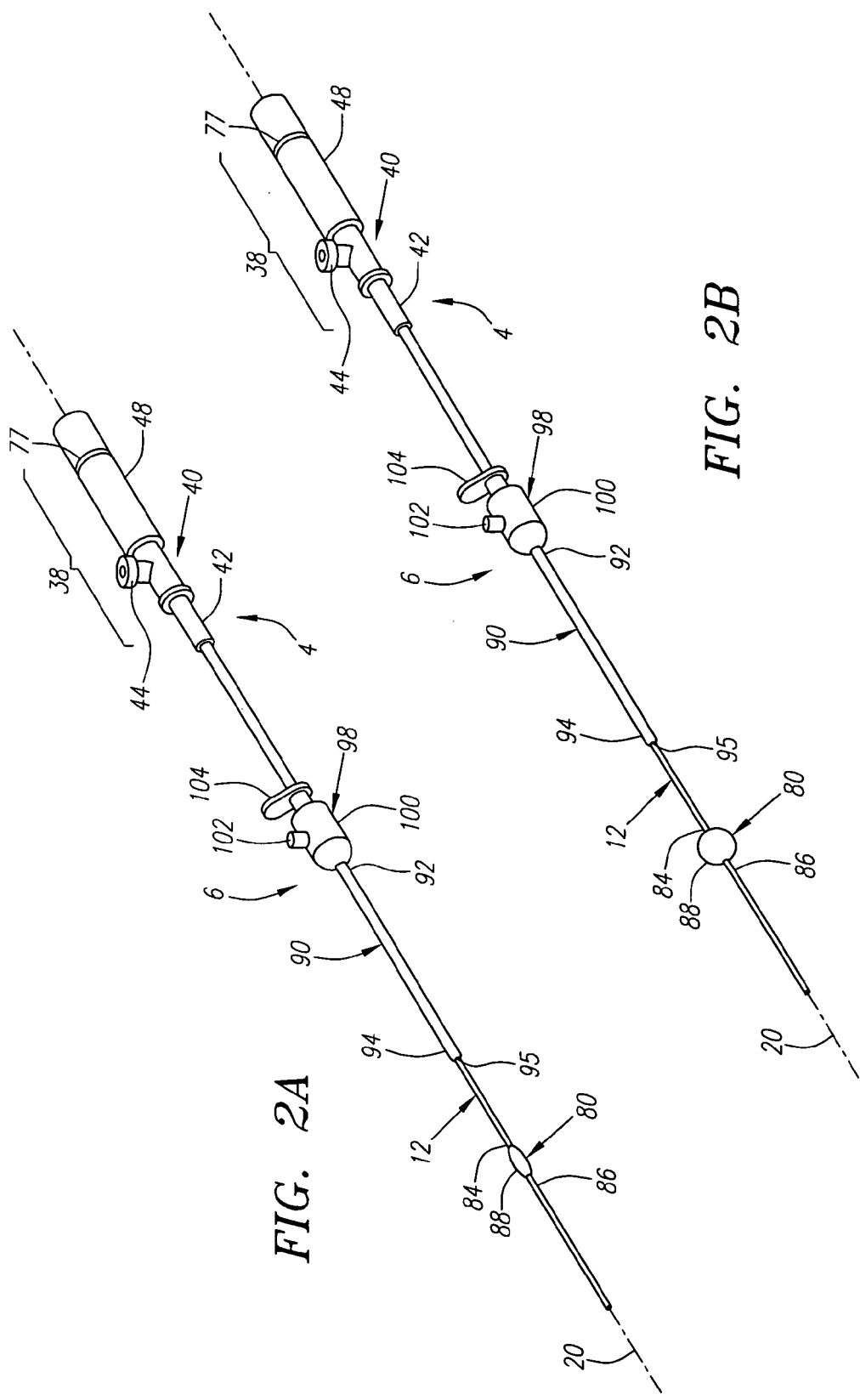

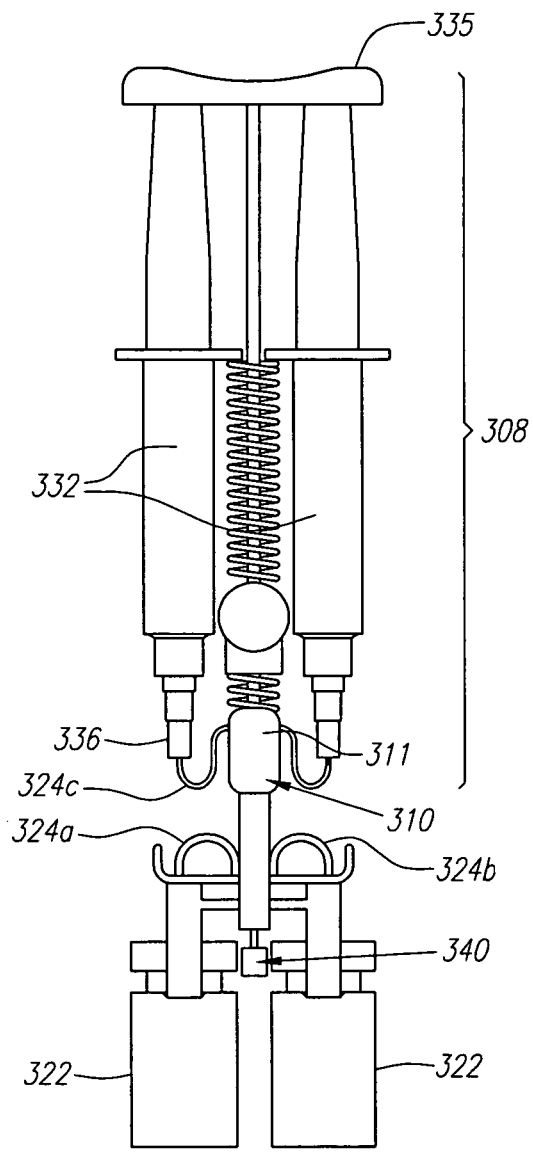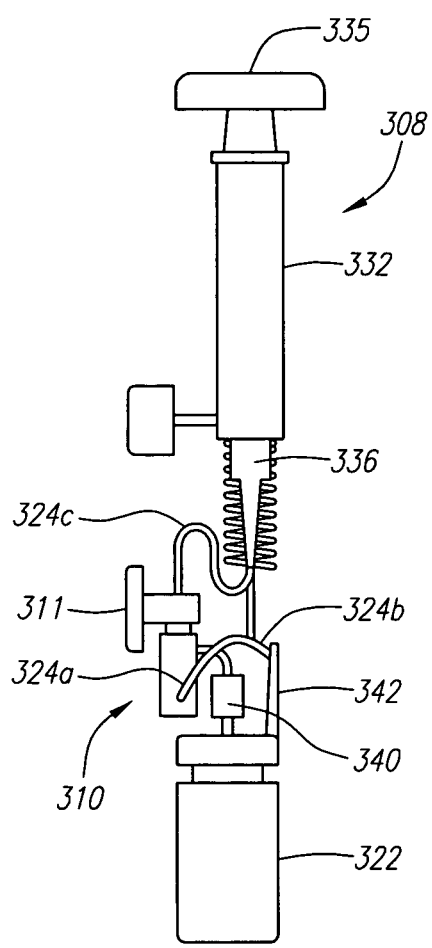
FIG. 16A
FIG. 16B

AUTO-RETRACTION APPARATUS AND METHODS FOR SEALING A VASCULAR PUNCTURE

RELATED APPLICATION DATA

This application is a continuation-in-part of application Ser. No. 10/454,362, now U.S. Pat. No. 7,331,979, filed Jun. 4, 2003, the disclosure of which is expressly incorporated herein by reference.

FIELD OF INVENTION

The present invention relates generally to apparatus and methods for sealing punctures through tissue and, more particularly, to apparatus and methods for sealing a vascular puncture extending through tissue into a blood vessel, and to apparatus and methods for delivering a sealing compound into a percutaneous puncture extending from a patient's skin to a blood vessel or other body lumen to seal the puncture.

BACKGROUND

Apparatus and methods are known for accessing a patient's vasculature percutaneously to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators. A catheter or other device may be advanced through the introducer sheath and over the guide wire into a position for performing a medical procedure. In this manner, the introducer sheath may facilitate introducing various instruments into the vessel, while minimizing trauma to the vessel wall and/or minimizing blood loss. Upon completing the procedure, the instrument(s) and introducer sheath may be removed, leaving a puncture extending between the skin and the vessel.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in an operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a collagen plug that may be delivered into a puncture through tissue. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon, thereby preventing the plug from entering the vessel. Once the plug is positioned within the puncture, the balloon may be deflated and withdrawn, leaving the plug therein to expand and seal the puncture and/or to promote hemostasis.

By way of another example, U.S. Pat. Nos. 5,192,302 and 5,222,974 issued to Kensey et al. describe a biodegradable collagen plug that may be delivered through an introducer sheath into a puncture site. The disclosed plug, however, may be difficult to position properly with respect to the vessel, which may be significant since it is generally undesirable to expose the collagen material within the bloodstream where it may float downstream and cause an embolism.

SUMMARY OF THE INVENTION

The present invention is generally directed to apparatus and methods for sealing a puncture in a body, including without limitation, apparatus and methods for providing temporary or permanent hemostasis within a vascular puncture extending into a blood vessel, and/or to apparatus and methods for delivering a sealing compound into a percutaneous puncture extending from a patient's skin to a blood vessel or other body lumen.

In one embodiment, an apparatus is provided for sealing a puncture through tissue that includes an introducer sheath, delivery sheath, or other tubular member, an occlusion member, and a retraction assembly. The tubular member may include a proximal end, a distal end having a size for insertion into the puncture, and a lumen extending between the proximal and distal ends. The occlusion member may be slidably disposed within the tubular member and may include a proximal end, a distal end extending distally through an opening in the distal end of the tubular member, and an expandable member on the distal end.

The retraction assembly may be coupled to the tubular member and the occlusion member for controlling axial movement of the tubular member relative to the occlusion member. The retraction assembly may include a lock for securing the tubular member in a distal position relative to the occlusion member, and a release or trigger for disengaging the lock, the retraction assembly being biased to retract the tubular member proximally relative to the occlusion member when the lock is disengaged.

The apparatus may also include a delivery device communicating with the proximal end of the tubular member. The delivery device may include one or more plungers that are advanceable to deliver sealing compound into the lumen, the plunger(s) configured for triggering the release when the plunger(s) is(are) advanced to deliver the liquid sealing compound.

In another embodiment, a method is provided for sealing a puncture communicating with a body lumen using an apparatus that includes an occlusion member including an expandable member on a distal end thereof, an introducer sheath, delivery sheath, or other tubular member, and a retraction assembly coupled to the occlusion member. The tubular member may be introduced into the puncture, e.g., a percutaneous puncture communicating with a blood vessel or other body lumen. The occlusion member may be introduced through the tubular member into the puncture with the expandable member in a collapsed state until the expandable member is disposed within the body lumen.

The tubular member may be coupled to the retraction assembly, e.g., by connecting a sheath or shaft extending from the retraction assembly to a proximal end of the tubular member. The expandable member may be expanded, and the occlusion member may be at least partially withdrawn from the puncture until the expandable member substantially seals the puncture from the body lumen.

A sealing compound may be introduced through the tubular member into the puncture until the retraction assembly is triggered whereupon the tubular member may be automatically withdrawn at least partially from the puncture, thereby delivering the sealing compound along the puncture. The sealing compound may be delivered from one or more syringes into the tubular member when a plunger assembly of the syringe(s) is depressed. The plunger assembly may include a trigger for releasing a lock member of the retraction assembly when the plunger assembly is depressed a predetermined distance. Where the tubular member is coupled to the retraction assembly by connecting a sheath or shaft extending from the retraction assembly, the sheath or shaft may be biased to move proximally when the lock member of the retraction assembly is released, thereby withdrawing the tubular member at least partially from the puncture, e.g., as the sealing compound is delivered.

Thereafter, the expandable member may be collapsed, and the occlusion member may be withdrawn from the puncture. The sealing compound may include a liquid sealing compound, and the occlusion member may be removed from the puncture after the liquid sealing compound has at least partially solidified.

In yet another embodiment, a method is provided for sealing a puncture communicating with a body lumen using an apparatus that includes an occlusion member including an expandable member on a distal end thereof, a delivery sheath, introducer sheath, or other tubular member sheath slidable along the occlusion member, and a retraction assembly coupled to the occlusion member and the tubular member. The tubular member and the occlusion member may be introduced into the puncture, e.g., simultaneously or sequentially.

For example, the occlusion member may be disposed within the tubular member such that the occlusion member is introduced into the puncture when the tubular member is introduced into the puncture. Alternatively, the occlusion member may be introduced into the puncture through the tubular member after the tubular member is introduced into the puncture.

If the occlusion member is introduced after the tubular member, the tubular member may be coupled to the retraction assembly after the occlusion member is introduced into the puncture through the tubular member. For example, a sheath may overlie a portion of the occlusion member that may be coupled to the proximal end of the tubular member Alternatively, if the occlusion member and tubular member are introduced simultaneously, the tubular member may be coupled to the retraction assembly before introduction.

For example, the occlusion member may be introduced into the puncture with the expandable member in a collapsed state until the expandable member is disposed within the body lumen beyond the distal end of the tubular member. The expandable member is then expanded, and the occlusion member is at least partially withdrawn from the puncture until the expandable member substantially seals the puncture from the body lumen.

A sealing compound may be introduced through the tubular member into the puncture until the retraction assembly is triggered whereupon the tubular member may be automatically withdrawn at least partially from the puncture, thereby delivering the sealing compound along the puncture.

In still another embodiment, an apparatus is provided for delivering a sealing compound into a puncture extending through tissue that includes one or more barrels, e.g., a pair of barrels, a plunger assembly, and an auto-injection assembly. Each barrel includes a chamber for storing a component of the sealing compound, and an access port communicating with the chamber. A plunger assembly including a piston slidable within each barrel chamber from a proximal position to a distal position for delivering the components out of the barrel chambers through the respective ports.

An auto-injection assembly is coupled to the plunger assembly that includes a spring mechanism that is locked in an inactive condition, and an actuator coupled to the spring mechanism. When the spring mechanism is inactive, the plunger assembly may be manipulated manually, e.g., to load sealing components into the barrels. When the actuator is activated, the spring mechanism is released, whereupon the spring mechanism may direct the pistons of the plunger assembly towards their distal positions to deliver the components out of the barrel chambers.

Optionally, the apparatus may include a valve coupled to the barrel ports for selectively placing the barrel chambers in communication with one or more inlet lines and one or more outlet lines. For example, the valve may be movable to a first or loading position in which the barrel chambers are in communication with the inlet line, e.g., to deliver further components from a container or other source, e.g., for mixing the sealing components in the barrel chambers with the further sealing components and/or for loading sealing components into the barrels. The valve may also be movable to a second or delivery position wherein the barrel ports communicate with a "Y" fitting, mixer, and/or tubing, e.g., for mixing together the sealing components injected from the barrels and/or delivering the sealing components into a puncture. Optionally, the valve may also be moved to a third or closed position wherein the barrel ports are isolated to prevent the sealing components from escaping.

In yet another embodiment, a method is provided for delivering a sealing compound from a delivery device that includes a plurality of barrels and a plunger assembly including pistons slidable within the barrels between first and second positions.

Sealing components may be provided in the barrels with the plunger assembly in the first position. For example, a valve coupled to the barrels may be moved to a first position wherein the barrels communicate with a container or other source of further sealing components. The plunger assembly may be manually advanced into the barrels to deliver the sealing components in the barrels into the containers to mix the sealing components with the further sealing components. For example, the barrels may include one or more buffer solutions, and the containers may include powdered or other solid forms of polymer precursor compounds. Once the components are mixed, e.g., by shaking the containers, the plunger assembly may be manually withdrawn from the barrels to draw mixed sealing components from the containers into the barrels.

When it is desired to deliver the sealing compound, an actuator coupled to a spring mechanism may be activated, whereupon the spring mechanism may direct the plunger assembly to move towards the second position to deliver the sealing components out of the barrels. For example, a valve coupled to the barrel ports may be moved to a delivery position, wherein the ports communicate with an introducer sheath, delivery sheath, or other tubular member placed within a puncture. When the actuator is activated, the sealing compounds may be delivered through the tubular member and into the puncture, e.g., via an introducer, delivery sheath, or other tubular member. Optionally, the sealing components in the barrels may mix in a "Y" fitting, a mixer, and/or within the tubular member itself before being delivered into the puncture.

In still another embodiment, an occlusion apparatus is provided for sealing a puncture extending from a patient's skin through tissue to a body lumen, e.g., for temporary hemostasis. The apparatus may include an outer member including a proximal end, a distal end having a size and shape for insertion into a puncture, and a lumen extending between the proximal and distal ends, thereby defining a longitudinal axis therebetween. An inner member may be slidably disposed within the lumen of the outer member that also includes proximal and distal ends.

The apparatus may include an expandable member that includes a proximal end coupled to the distal end of the outer member and a distal end coupled to the distal end of the inner member. In one embodiment, an interior of the expandable member may communicate with the lumen of the outer member, the expandable member being expandable when fluid is introduced into the interior. In another embodiment, the expandable member may include a frame that expands when the inner member is directed proximally relative to the outer member.

The apparatus may include a housing on the proximal end of the outer member that includes a piston slidably disposed within a chamber and coupled to the inner member, and a reservoir filled with inflation media communicating with the chamber. The housing includes an actuator, e.g., a depression switch coupled to another piston, that may be activated by a user to direct the inflation media from the reservoir into the chamber.

If the expandable member is inflatable, the reservoir and/or chamber communicate with the lumen of the outer member, and consequently with the interior of the expandable member. When the actuator is activated, the expandable member is expanded substantially simultaneously with the piston being directed proximally to pull the inner member proximally and shorten the expandable member as it expands. If the expandable member includes an expandable frame, when the actuator is activated, the piston pulls the inner member proximally, causing the frame to buckle and/or otherwise expand, thereby extending a membrane thereon substantially transversely. The actuator may be deactivated to withdraw the inflation media from the chamber and/or the lumen into the reservoir, thereby substantially directing the piston distally to push the inner member distally and collapsing the expandable member.

In yet another embodiment, an apparatus is provided for sealing a puncture extending from a patient's skin to a body lumen. The apparatus may include a tensioner and an elongate occlusion member. The occlusion member may include a proximal end, a distal end insertable into the puncture, and an expandable member on the distal end of the occlusion member that may be disposed within the body lumen while the proximal end remains outside the puncture. The tensioner may include an elongate body with a foot on a first end thereof and a saddle on a second end thereof, the foot having a shape for placement against the patient's skin adjacent the puncture. The saddle may be moveable along or otherwise relative to the shaft towards the foot and biased to move away from the foot. Cooperating connectors may be provided on the foot and the proximal end of the occlusion member for securing the occlusion member to the saddle.

During use, a distal end of the occlusion member may be introduced into the puncture with an expandable member thereon in a collapsed state until the expandable member is disposed within the body lumen, whereupon the expandable member may be expanded to an expanded state within the body lumen. A foot of the tensioner may be placed against the patient's skin adjacent the puncture, and the saddle may be directed towards the foot to reduce a distance between the saddle and the foot. The saddle may be connected to a proximal end of the occlusion member, whereupon the saddle may be released to automatically (e.g., using spring-activated forces) move away from the foot. Thus, a proximal force may be applied to the occlusion member to hold the expandable member against a wall of the body lumen and substantially seal the puncture from the body lumen, e.g., to provide temporary hemostasis before and/or during injection of sealing compounds into the puncture.

Other embodiments, aspects, and features of the present invention will become apparent from consideration of the following description taken in conjunction with the accompanying drawings.

BRIEF DESCRIPTION OF THE DRAWINGS

The figures illustrate the design and utility of exemplary embodiments of the invention, which are shown for purposes of illustration and not limitation, in which:

FIG. 1 is a perspective view of an apparatus for sealing a puncture through tissue including an introducer sheath, an occlusion member, a retraction assembly, and a source of liquid sealing compound.

FIGS. 2A and 2B are perspective views of the introducer sheath and occlusion member of FIG. 1, showing a balloon on the occlusion member in collapsed and expanded states, respectively.

FIG. 16A is a front view of a syringe assembly connected to a linear valve, such as that shown in FIG. 15, with the valve in a first position connecting the syringe assembly to vials or precursor polymer compounds.

FIG. 16B is a side view of the syringe assembly of FIG. 16A, with the linear valve in a second position connecting the syringe assembly to a "Y" fitting.

DETAILED DESCRIPTION OF THE ILLUSTRATED EMBODIMENTS

Figure 3A:
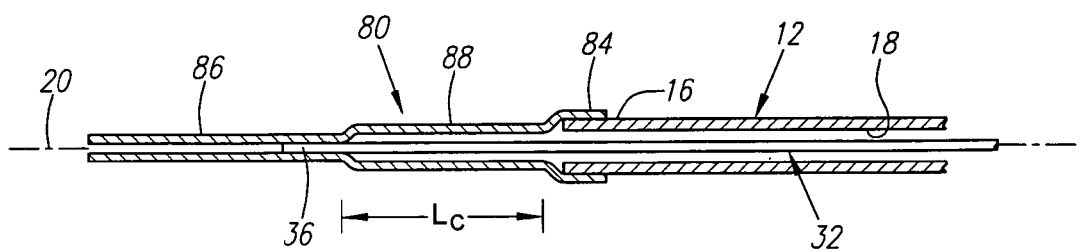
FIGS. 3A and 3B are cross-sectional details of a distal portion of the occlusion member shown in FIGS. 2A and 2B, respectively.

FIGS. 1-6 depict an exemplary embodiment of an apparatus 2 for sealing a puncture extending through tissue and/or communicating with a body lumen (not shown). Generally, the apparatus 2 includes an occlusion member 4 carrying a balloon 80 or other expandable member, an introducer sheath assembly 6 slidable relative to the occlusion member 4, a delivery device 8 for delivering sealing material through the introducer sheath assembly 6, and a retraction assembly 10 for controlling movement of the introducer sheath assembly 6 relative to the occlusion member 4.

Turning to FIGS. 1, 2A, and 2B, the introducer sheath assembly 6 generally includes an outer sleeve or introducer sheath 90 including a proximal end 92, a distal end 94, and a housing 98 on the proximal end 92 defining a cavity 99. The introducer sheath 90 may be an elongate tubular member including a lumen 96 (not shown, see FIGS. 11A-11E) that extends between the proximal and distal ends 92, 94. Preferably, the introducer sheath 90 terminates in a tapered distal tip 95 for facilitating advancing the introducer sheath 90 through a puncture. Exemplary materials for the introducer sheath 90 may include plastics, such as polyamide, PEEK, nylon, PET, PEBAX, and polyethylene, metals, such as stainless steel, and nickel titanium, and/or composite materials.

The housing 98 may include a generally annular body 100 attached or otherwise coupled to the proximal end 92 of the introducer sheath 90. The housing 98 may include one or more side ports 102 that communicate with the cavity 99 and the lumen 96 of the introducer sheath 90. A single side port 102 is provided that may include a luer lock or other connector, e.g., to facilitate connecting tubing 106 and the like to the side port 102. In addition, the housing 98 may include a flange 104 or other connector (not shown) that may be used to couple the introducer sheath assembly 6 to the retraction assembly 8, as described further below. Alternatively, the introducer sheath 90 may be a conventional introducer sheath, such as those well known in the art.

The introducer sheath assembly 6 is configured for slidably receiving the occlusion member 4 therein, as described further below. For example, the occlusion member 4 may be inserted through the lumen 96 of the introducer sheath 90 such that the balloon 80 is disposed distally beyond the distal end 94 of the introducer sheath 90. From this distal position, the introducer sheath assembly 6 may be slidable proximally relative to the occlusion member 4, e.g., to facilitate delivering sealing material around the occlusion member 4, as shown in FIGS. 11A-11F and described further below. The occlusion member 4 and introducer sheath assembly 6 may include cooperating detents, connectors, or other features (not shown) that may interact to limit relative movement of the introducer sheath assembly 6 relative to the occlusion member 4. For example, the introducer sheath assembly 4 may be slidable along the occlusion member 4, and the cooperating features may prevent the distal end 96 of the introducer sheath 90 from being moved closer to the balloon 80 than a desired minimum distance, e.g., not more than about five millimeters (5 mm), as explained further below.

To substantially seal the introducer sheath assembly 6 around the outer member 12 of the occlusion member 4, the housing 98 may include one or more annular seals (not shown) that provide a fluid-tight seal around the outer member 12 (or other instruments, not shown, inserted into the introducer sheath assembly 6) yet allow the introducer sheath assembly 6 to slide along the outer member 12. Thus, when fluids are delivered into the housing 98 from the side port 102, the seals 99 may prevent the sealing compound from leaking out of the housing 98, and instead the fluids may pass through the lumen 96 of the introducer sheath 90, as described further below.

As best seen in FIGS. 2A, 2B, 3A, and 3B, the occlusion member 4 is an elongate structure including an outer member 12, an inner member 32 slidably coupled to the outer member 12, and a hub subassembly 38 or other mechanism for biasing the inner member 32 relative to the outer member 12. The balloon 80 or other expandable member (not shown) is carried by the occlusion member 4, and preferably coupled to the inner and outer members 32, 12, as described more particularly below. Although exemplary embodiments of the occlusion member 4 are described herein, additional information on structures and operation of an occlusion member that may be included in the apparatus 2 are disclosed in above-incorporated application Ser. No. 10/454,362.

The outer member 12 may be an elongate tubular body including a proximal end 14, a distal end 16, and a lumen 18 extending therebetween (shown in FIGS. 3A, 3B, and 5), thereby defining a longitudinal axis 20. The outer member 12 may be flexible, semi-rigid, or rigid, e.g., having a uniform or variable flexibility along its length. A proximal portion of the outer member 12 may be substantially rigid, e.g., a section of hypotube (not shown), to facilitate advancing the occlusion member 4 through a tubular member, such as the introducer sheath assembly 6. Optionally, a lubricious coating (not shown) may be provided on the exterior of the outer member 12.

In one embodiment, the distal end 16 is substantially flexible such that the distal end 16 may curve, bend, prolapse, or otherwise conform substantially to the contour of a puncture and/or other body lumen (not shown) into which the distal end 16 is inserted. In other embodiments, such as those described below, the distal end 16 may include detents, seals, and/or other components (not shown) to facilitate cooperation with the introducer sheath assembly 6. The distal end 16 of the outer member 12 may have a size sufficient to be inserted into a relatively small puncture and/or body lumen. For example, the distal end 16 (and possibly the remainder of the outer member 12) may have an outer diameter between about 0.010-0.030 inch (0.25-0.75 mm), and less than about 0.020 inch (0.5 mm) in certain embodiments.

The inner member 32 may be an elongate body including a proximal end 34 (shown in FIGS. 5 and 6), and a distal end 36.

Figure 3B:
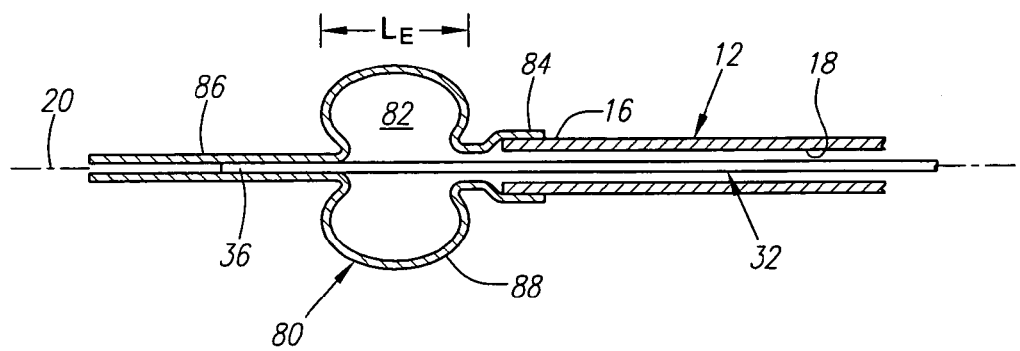

As best seen in FIGS. 3A and 3B, the inner member 32 may be slidably received within the lumen 18 of the outer member 12 such that the distal end 36 of the inner member 32 extends beyond the distal end 16 of the outer member 12. Preferably, the inner member 32 is sufficiently small such that the inner member 32 may be received in the lumen 18 of the outer member 12, yet accommodate fluid being delivered through the lumen 18, i.e., along an exterior of the inner member 32. The inner member 32 may be a solid wire of nickel-titanium alloy ("Nitinol"), stainless steel, polymeric, and/or composite material having an outer diameter between about 0.003-0.020 inch (0.075-0.5 mm), and less than about 0.010 inch (0.25 mm) in certain embodiments. Alternatively, the inner member 32 may include a lumen (not shown) for receiving a guidewire (not shown) therethrough, e.g., such that the occlusion member 4 may be advanced over a guidewire.

Figure 4:
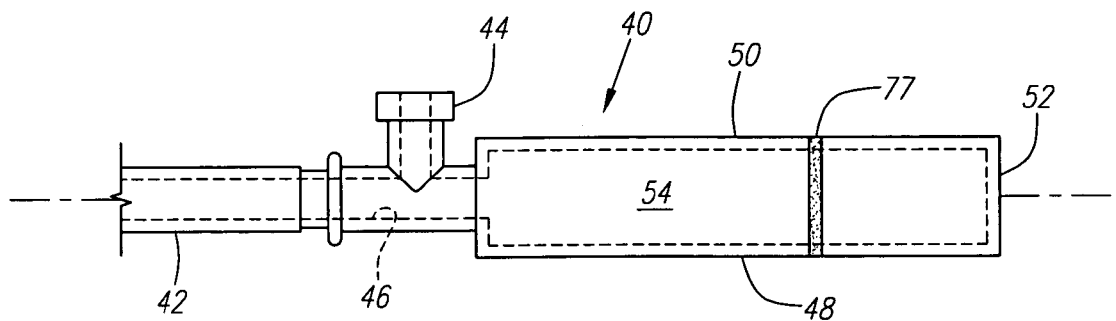
FIG. 4 is a side view of a hub subassembly shown on a proximal end of the occlusion member of FIGS. 2A and 2B.
Figure 5:
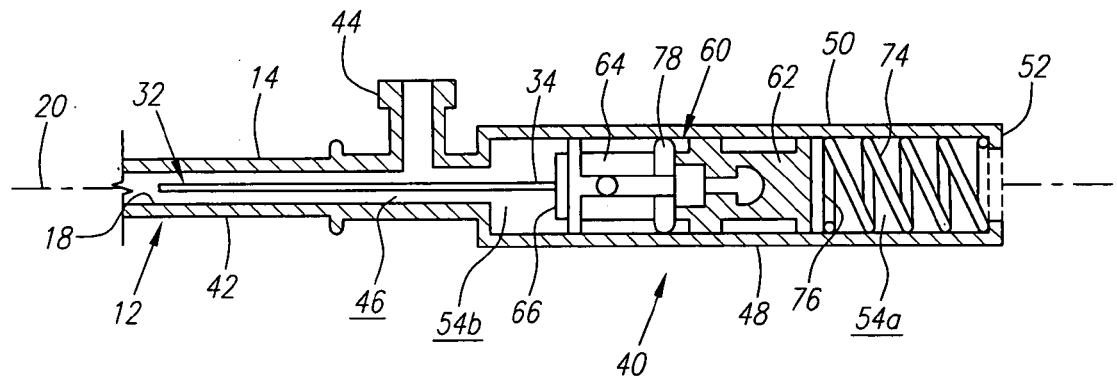
FIG. 5 is a cross-sectional side view of the proximal hub subassembly of FIG. 4, including a piston and spring therein and connected to inner and outer members of the occlusion member.
Figure 6:
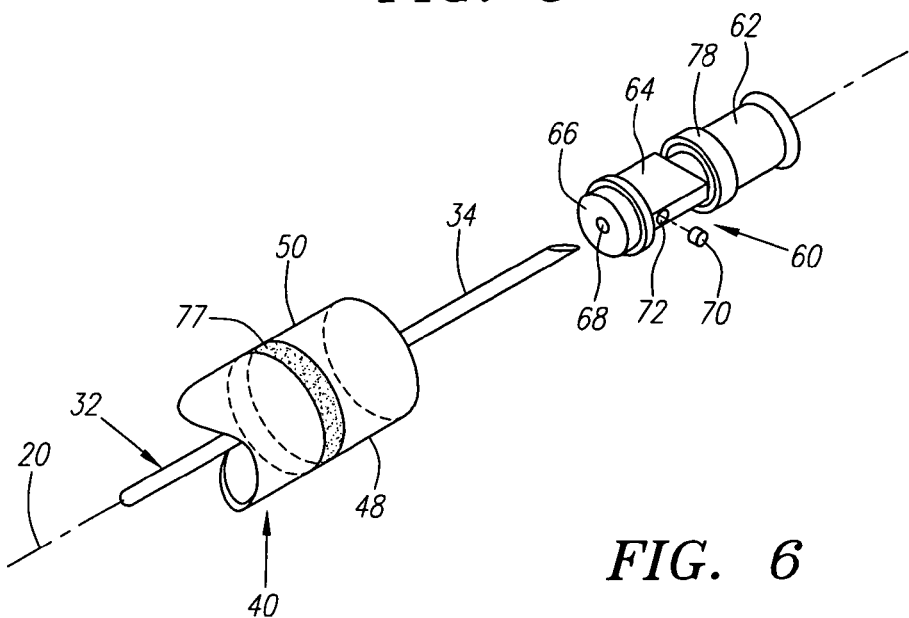
FIG. 6 is a perspective detail, showing a piston being attached to an inner member and received in a housing to provide the proximal hub subassembly shown in FIGS. 4 and 5.

The inner member 32 may be biased to move distally relative to the outer member 12, i.e., from a proximal position (such as that shown in FIG. 3B) to a distal position (such as that shown in FIG. 3A), e.g., to facilitate collapsing the balloon 80. For example, as shown in FIGS. 4-6, hub subassembly 38 may be provided for biasing the inner member 32 relative to the outer member 12. Generally, the hub subassembly 38 may include a housing 40 extending proximally from the proximal end 14 of the outer member 12 and a piston 60 coupled to the proximal end 34 of the inner member 32. As best seen in FIG. 4, the housing 40 may include a hollow adaptor end 42, a side port 44 communicating with an interior 46 of the housing 40, and a hollow cylinder 48. The cylinder 48 may include an outer wall 50 and a proximal end wall 52, thereby defining a chamber 54 that communicates with the interior 46 of the housing 40. The end wall 52 may only partially enclose the chamber 54 or may substantially seal the chamber 54, as explained further below.

The adapter end 42 of the housing 40 may be attached to the proximal end 14 of the outer member 12 such that the interior 46 of the housing 40 communicates with the lumen 18 of the outer member 12. For example, the adapter end 42 may be attached to the proximal end 14 of the outer member 12 using an adhesive, an interference fit, mating threads, and/or other connectors, e.g., to substantially permanently attach the housing 40 to the proximal end 14 of the outer member 12. With the housing 40 attached to the outer member 12, the side port 44 may communicate with the lumen 18 via the interior 46 of the housing 40. Thus, fluid delivered into the side port 44 may enter the lumen 18 as well as the chamber 54 of the cylinder 48 via the interior 46 of the housing 40.

The side port 44 may include a connector, e.g., a luer lock connector, or a nipple (not shown) for connecting tubing or otherwise connecting a source of fluid or other inflation media to the side port 44. For example, a syringe filled with inflation media, e.g., saline, carbon dioxide, and the like (not shown), may be connected to the side port 44 for manually delivering the inflation media into the lumen 18. Alternatively, a pump or other device (also not shown) may be provided for delivering fluid at a desired pressure and/or flow rate.

As best seen in FIG. 5, the piston 60 may be slidably received in the cylinder 48, thereby dividing the chamber 54 into a proximal chamber 54a and a distal chamber 54b. The piston 60 may include one or more seals 62 for providing a fluid-tight seal between the piston 60 and the side wall 50 of the cylinder 48, while accommodating the piston 60 sliding within the chamber 54. The piston 50 may include a distal surface 66 that is exposed to fluid pressure within the distal chamber 54b, and consequently to fluid pressure within the interior 46 of the housing 40 and/or within the lumen 18 of the outer member 12.

The proximal end 34 of the inner member 32 may be coupled to the piston 60, thereby coupling axial movement of the inner member 32 to axial movement of the piston 60, as shown in FIG. 5. For example, as shown in FIG. 6, the distal surface 66 of the piston 50 may include an aperture 68 through which the proximal end 34 of the inner member 32 may be received. Once the inner member 12 is inserted a desired distance into the aperture 68, the inner member 12 may be secured to the piston 60 using known mechanisms, such as a set screw 70 and/or adhesive.

To provide a biasing force, e.g., to facilitate returning the occlusion member to a minimum profile, a compression spring or other mechanism 74 may be provided in the proximal chamber 54a of the housing 40, e.g., for biasing the piston 60 away from the end wall 52, i.e., towards the adapter end 42 of the housing 40. The spring 74 may apply an axial force against a proximal surface 76 of the piston 60 and the end wall 52 of the cylinder 48. The spring constant of the spring 74 may be selected to provide a desired biasing force.

In an alternative embodiment, the proximal chamber 46a of the cylinder 48 may be filled with a compressible fluid, e.g., nitrogen, carbon dioxide, or air, that may be pressurized to a predetermined pressure to bias the piston 50 away from the end wall 44. As fluid is introduced into the distal chamber 46b, the pressure of the fluid may exceed the predetermined pressure, thereby causing the piston 60 to move proximally and compress the fluid within the proximal chamber 46a until the pressures within the chambers 46a, 46b are substantially equal to one another. In another alternative embodiment, an extension spring (not shown) may be provided in the distal chamber 54b that may be coupled to the piston 60 and the cylinder 48 at the end near the side port 44 to bias the piston 60 distally.

In yet another alternative, the hub subassembly 38 may not include a biasing mechanism, e.g., no spring 74 or compressible fluid. Instead, movement of the piston 60 may be controlled directly by the pressure and/or vacuum applied to inflate and/or deflate the balloon 80, respectively. For example, when a substantially incompressible fluid is delivered into the lumen 18 of the outer member 12, the pressure differential between the piston 60 and the balloon 80 may initially cause the piston 60 to slide proximally, thereby applying a proximal tensional load to the inner member 32 while the balloon 80 is expanding. When a negative pressure (vacuum) is applied to evacuate the fluid from the lumen 18 and deflate the balloon 80, the negative pressure differential between the piston 60 and the balloon 80 may initially cause the piston 60 to slide distally, thereby applying a distal compressive load to the inner member 32 while the balloon 80 is deflating.

A desired pressure differential may be achieved by using a viscous fluid (i.e., a fluid more viscous than air) and/or by creating a restriction (not shown) within the lumen 18 distal to the side port 44 to delay the pressure from entering or exiting the balloon 80. This pressure differential may be particularly important when inflating and/or deflating an everted balloon. In addition, or alternatively, a constriction (not shown) may be provided within the lumen 18, e.g., between the side port 44 and the distal end 16 to cause the piston 60 to move before fluid is introduced into the balloon 80. Optionally, cooperating stops (not shown) may be provided for preventing over-inflation of the balloon 80, as described in application Ser. No. 10/454,362 incorporated by reference herein.

Returning to FIGS. 1-3B, the balloon 80 is carried on the distal end 16 of the outer member 12. Generally, the balloon 80 may be expandable from a collapsed state (shown in FIGS. 2A and 3A) to an expanded state (shown in FIGS. 2B and 3B) when a fluid or other inflation media (not shown) is introduced into an interior 82 of the balloon 80. In an alternative embodiment, other expandable members, e.g., a mechanically expandable or self-expanding member (not shown) may be provided instead of the balloon 80, as described further below.

The balloon 80 may be formed from a flexible, substantially inelastic material, e.g., a nonelastomeric material, such as PET, nylon, polyethylene, polyurethane, PEBAX, and the like, that may provide a substantially noncompliant or semi-compliant balloon 80 that may expand to a predetermined size once a minimum pressure is introduced into the interior 82. In this embodiment, the size of the balloon 80 in the expanded state may be fixed. Alternatively, the balloon 80 may be formed from an elastic material, such that the size of the balloon 80 in the expanded state is dependent upon the pressure or volume of fluid delivered within the interior 82, as is known in the art.

The balloon 80 may include a proximal end 84, a distal end 86, and an expandable intermediate section 88 defining the interior 82 of the balloon 80. The proximal end 84 of the balloon 80 may be attached to the distal end 16 of the outer member 12, and the distal end 86 of the balloon 80 may be attached to the distal end 36 of the inner member 32. When the proximal end 84 of the balloon 80 is attached to the outer member 12, the interior 82 of the balloon 80 may communicate with the lumen 18 of the outer member 12. Alternatively, the proximal end 84 of the balloon 80 may extend proximally, replacing all or a portion of the outer member 12 (not shown). In a further alternative, the proximal end 84 of the balloon 80 may be laminated or drawn over a stiffer proximal shaft (not shown).

As best seen in FIGS. 3A and 3B, the proximal end 84 of the balloon 80 may overlie and be attached to the distal end 16 of the outer member 12, e.g., using an adhesive, sonic welding, crimping, an interference fit, and the like. The distal end 36 of the inner member 32 may extend through the interior 82 of the balloon 80 (i.e., through the intermediate section 88), and at least partially into the distal end 86 of the balloon 80, optionally extending an entire length of the distal end 86 of the balloon 80. Similar to the proximal end 84, the distal end 86 of the balloon 80 may be attached to the distal end 36 of the inner member 32, e.g., using an adhesive, sonic welding, crimping, a compressive sleeve, an interference fit, and the like.

An annular band of material, e.g., polyimide or PET, may be attached or otherwise provided over the proximal and distal ends 84, 86 of the balloon 80 to attach the ends 84, 86 to the outer and inner members 12, 32. For example, a band may be provided around the proximal end 84 of the balloon 80 to prevent the balloon 80 from delaminating from the outer member 12 when the balloon 80 is inflated.

The distal end 86 of the balloon 80 may extend beyond the distal end 36 of the inner member 32, e.g., to provide a floppy or otherwise substantially atraumatic tip for the occlusion member 4. For example, the distal end 86 of the balloon 80 may have a length of at least about fifty millimeters (50 mm), and the distal end 36 of the inner member 32 may only extend about twenty millimeters (20 mm) or less into the distal end 86 of the balloon 80. Alternatively, the distal end 36 of the inner member 32 may extend beyond the distal end 86 of the balloon 80, and may terminate in a substantially atraumatic tip (not shown). The atraumatic tip may mimic the behavior of a standard "J"-tip guide wire, e.g., a 0.035 inch or 0.038 inch wire, commonly used with introducer sheaths.

In the collapsed state, shown in FIGS. 2A and 3A, the balloon 80 may conform substantially to the diameter of the outer member 12. Preferably, the proximal and distal ends 84, 86 of the balloon 80 and the distance between the distal ends 16, 36 of the outer and inner members 12, 32 are such that the balloon 80 is under slight axial tension in the collapsed state, thereby minimizing risk of the balloon 80 expanding, kinking, or otherwise increasing in cross-section and/or catching on anything contacted by the balloon 80.

The balloon 80 is expanded to the expanded state, shown in FIGS. 2B and 3B, by introducing inflation media (not shown) into the lumen 18 of the outer member 12, and consequently into the interior 82 of the balloon 80. As explained above, when fluid is introduced into the lumen 18, the fluid initially enters the interior 46 of the housing 40 (not shown, see FIGS. 4 and 5), and consequently into the distal chamber 54b of the cylinder 48 (also not shown, see FIGS. 4 and 5). As the fluid pressure within the distal chamber 54b exceeds the bias of the spring 74 (or other biasing mechanism), the piston 60 may move proximally within the cylinder 48, thereby pulling the inner member 32 proximally.

As best seen in FIGS. 3A and 3B, proximal movement of the inner member 32 relative to the outer member 12 causes the distal end 86 of the balloon 80 to move towards the proximal end 84 of the balloon 80. Thus, in the collapsed state, the intermediate section 88 of the balloon 80 may have a length $L_C$, while, in the expanded state, the intermediate section 88 may have a length $L_E$ that is substantially shorter than $L_C$. In the expanded state, the balloon 80 may have a diameter between about four and ten millimeters (4-10 mm), and a length $L_E$ between about two and ten millimeters (2-10 mm). For example, in an exemplary embodiment, the balloon may have a diameter of about six millimeters (6 mm) at thirty pounds per square inch (30 psi) internal pressure and a length $L_E$ of about four millimeters (4 mm).

In one embodiment, the balloon 80 at least partially everts in the expanded state, i.e., the length $L_E$ of the balloon 80 may be substantially smaller than the diameter. Stated differently, in the expanded state, the proximal and distal ends 84, 86 of the balloon 80 may become sufficiently close to one another that they at least partially enter the interior 82 of the balloon 80, as shown in FIG. 3B, thereby defining a toroidal shape. This everted configuration (which may also be referred to as a "bagel balloon" configuration) may facilitate creating hemostasis within a puncture in a wall of a body lumen (not shown) while allowing increased fluid flow and/or vessel perfusion to continue along the body lumen, as explained further below.

With reference to FIGS. 3A, 3B, and 5, the cross-section of the distal chamber 54b of the cylinder 48 may be substantially larger than a cross-section of the lumen 18 of the outer member 12. When a fluid is introduced into the side port 44 of the hub subassembly 38 under pressure, the pressure may impose a proximal force on the distal surface 66 of the piston 60. Because of the relatively large area of the distal chamber 54b, fluid may flow easily into the distal chamber 54b before flowing down the lumen 18 into the interior of the balloon 80. Thus, as fluid is introduced into the side port 44, a proximal force may be applied to the piston 60 before or as the balloon begins to expand, thereby shortening the balloon 80 before or as it expands towards the expanded state. Conversely, when fluid is evacuated out of the side port 44, the fluid from the distal chamber 54b of the cylinder 48 may be removed before fluid is drawn up the lumen 18 and the balloon 80 begins to collapse. The resulting vacuum may pull the piston 60 distally, causing the balloon 80 to elongate towards its collapsed length $L_C$ before or as the balloon collapses towards the collapsed state. This feature may be particularly useful for ensuring that the balloon 80 is collapsed to as small a profile as possible when the balloon 80 is collapsed from the expanded state to the collapsed state, e.g., to minimize disruption of any sealing compound deposited in the puncture as the balloon 80 is withdrawn, as explained elsewhere herein.

In alternative embodiments, other expandable members may be provided on the distal ends 16, 36 of the outer and/or inner members 12, 32. For example, instead of a single chamber balloon, as described above, a balloon may be provided that includes multiple chambers or "lobes" (not shown). Each lobe may be connected to the lumen 18 within the outer member 12 such that inflation media may enter each lobe to expand the balloon into a desired shape. Alternatively, the occlusion member 4 may include multiple lumens (not shown) that communicate with one or more lobes such that the lobes may be independently expanded, if desired. For example, the lobes may expand away from one another transversely relative to the longitudinal axis 20, thereby defining a relatively flat annular or "flower" configuration that may provide a substantially fluid-tight seal, yet allow perfusion to continue along a vessel, similar to the apparatus and methods described further below.

In other embodiments, mechanically expandable members may be provided, rather than fluid-expandable members. For example, an expandable frame (not shown) may be coupled to the distal ends 16, 36 of the outer and inner members 12, 32 that may be expanded as the inner member 32 is directed proximally relative to the outer member 12. A nonporous membrane may cover or otherwise be connected to the frame such that the membrane is expanded with the frame, thereby providing a relatively flat annular member that may be used to provided temporary hemostasis during delivery of a sealing compound, as described further below. Exemplary frames and membranes that may be used in conjunction with embodiments of the invention are described in U.S. Pat. Nos. 5,782,860, 5,922,009, 6,056,769, and 6,464,712, the disclosures of which are expressly incorporated by reference herein.

Figure 7A:
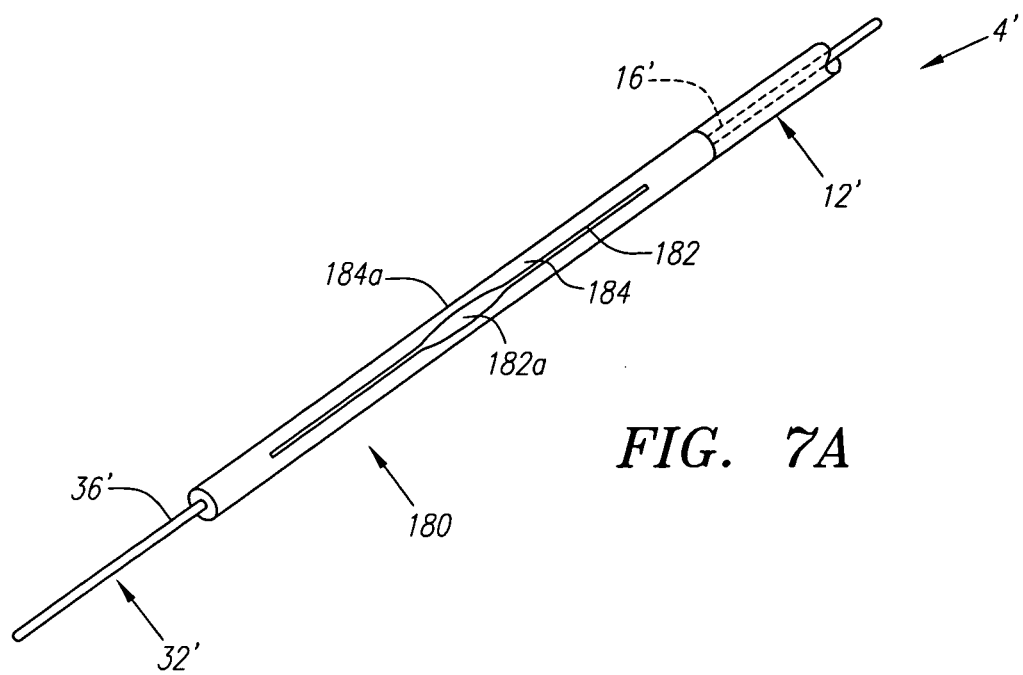
FIGS. 7A-7C are perspective views of an expandable frame that may be provided on an occlusion member.
Figure 7B:
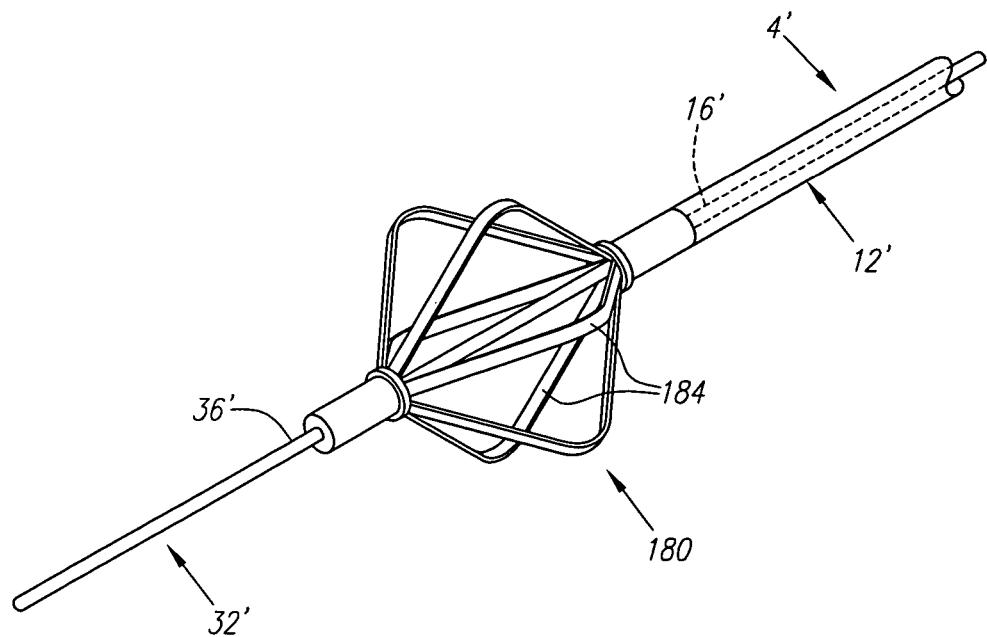
Figure 7C:
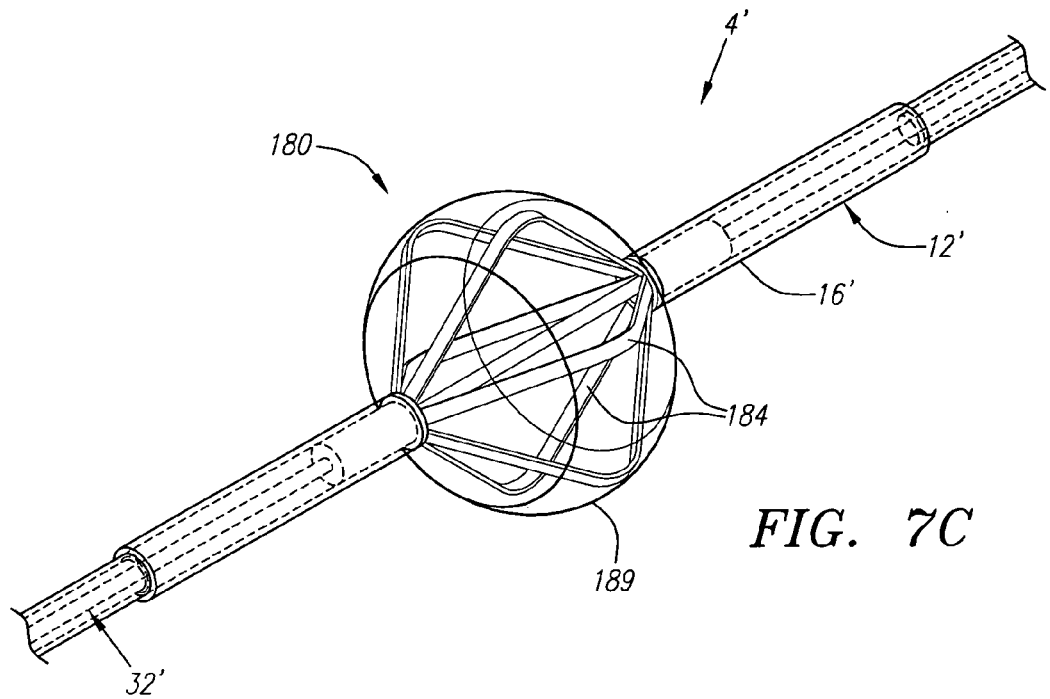

For example, FIGS. 7A-7C show an exemplary embodiment of an expandable frame 180 that may be provided on an occlusion member 4.' In FIG. 7C, a nonporous membrane 189 coupled to the frame 180 is shown in phantom, while in FIGS. 7A and 7B, the nonporous membrane 189 is omitted for convenience. The membrane 189 may cover all or a portion of the frame 180. For example, in one embodiment, the membrane 189 may only cover a proximal portion of the frame 180.

As shown in FIG. 7A, the frame 180 may be created by forming a plurality of longitudinal slits 182 in a tube, e.g., a Nitinol tube, using known procedures, such as laser cutting, to create struts 184 therebetween. Ends 186, 188 of the frame 180 may be coupled to respective distal ends 16,' 36' of the outer and inner outer members 12,' 32,' similar to the ends of the balloon 80 described above.

As shown in FIGS. 7B and 7C, as the inner member 32' is directed proximally relative to the outer member 12,' the struts 184 created by the slits 182 may buckle and expand transversely, to expand the membrane 189. Preferably, the slits 182 are formed to facilitate buckling of the struts 184. For example, as shown in FIG. 7A, an intermediate portion 182a of the slits 182 may be widened to provide a weak point 184a at which the struts 184 may buckle. Alternatively or in addition, the slits 182 may be curved at the intermediate portion 182a, e.g., defining a portion of a sinusoidal wave (not shown), to further control buckling of the struts 184, and/or to provide strain relief. The frame 180 and membrane 184 may be collapsed again by directing the inner member 32' distally relative to the outer member 12.'

To expand and/or collapse the frame 182, an actuator may be provided on the occlusion member 4.' For example, similar to the hub subassembly 38 described with respect to the balloon 80, a piston-cylinder arrangement may be provided on the proximal end 14' of the outer member 12' to direct the inner member 32' proximally and/or distally when a fluid is directed into the cylinder. In this embodiment, there would be no need for the fluid to flow down the lumen of the outer member 12' since expansion of the expandable frame 180 depends only upon the relative positions of the outer and inner members 12,' 32.'

Figure 8A:
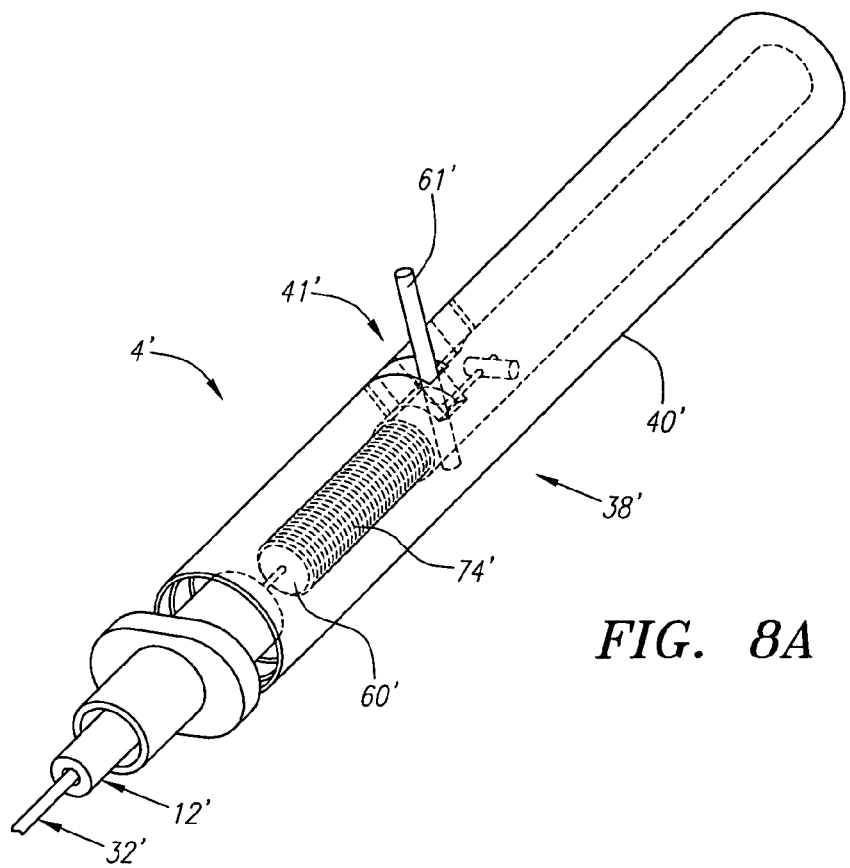
FIG. 8A is a perspective view of a switch for expanding and collapsing the expandable frame of FIGS. 7A-7C.
Figure 8B:
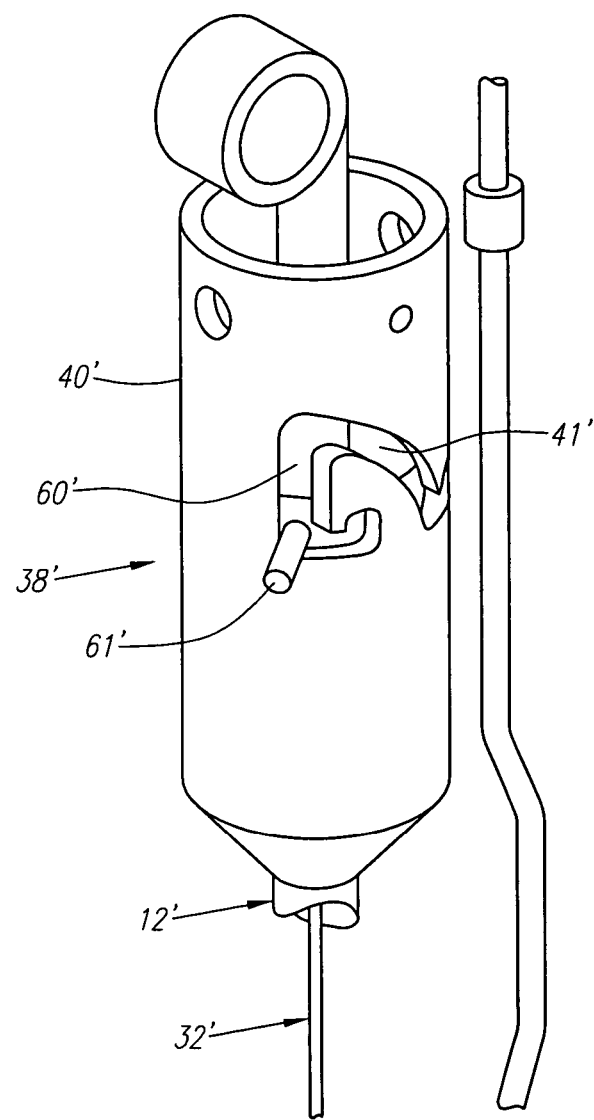
FIG. 8B is a detail of a pin-slot arrangement of the switch of FIG. 8A.

Alternatively, a mechanical switch 38' may be provided, such as that shown in FIGS. 8A and 8B. An outer housing 40' may be coupled to the proximal end 14' of the outer member 12,' and a piston 60' coupled to the inner member 32' and slidably disposed within the housing 40.' A pin 61' may be coupled to the piston 60' that extends through a "C" or "S" shaped slot 41' in the housing 40.' As shown in FIG. 8B, horizontal portions of the slot 41' may correspond to the proximal and distal positions in which the frame 182 (not shown, see FIGS. 7A-7C) is expanded and collapsed, respectively. The pin 61' may be slid horizontally out of one of the proximal and distal positions and moved along the slot 41' to the other position. Optionally, a spring or other mechanism may be provided for biasing the piston 60' distally or proximally, e.g., an extension spring 74' may be provided for biasing the frame 180 towards the collapsed state, similar to the fluid-activated mechanism described above.

In another alternative, the expandable frame may be biased to the expanded state, and a cover, e.g., a catheter, sheath, sleeve, and the like (not shown), may be provided for constraining the expandable frame in the collapsed state. For example, the struts of the expandable frame may be provided from a shape memory and/or superelastic material, e.g., Nitinol, that may be heat treated to the expanded state. The cover may extend along the outer member of the occlusion member, e.g., from the expandable frame towards the proximal end of the occlusion member.

Initially, e.g., during manufacturing and/or set-up, the cover may be directed over the expandable frame to resiliently force the struts to collapse towards the collapsed state. In the collapsed state, the occlusion member may be inserted into a puncture, e.g., through a delivery sheath or other tubular member, as described elsewhere herein. When it is desired to deploy the expandable frame, the cover may be at least partially retracted to expose the expandable frame, whereupon the struts may automatically expand towards the expanded state.

When it is desired to remove the occlusion member, the cover may be advanced back over the expandable frame to collapse the struts. Alternatively, the struts may be sufficiently resilient that the occlusion member may be removed without covering the expandable frame such that the struts contact the delivery sheath and collapse as they are drawn into the delivery sheath as the occlusion member is withdrawn.

Figure 12A:
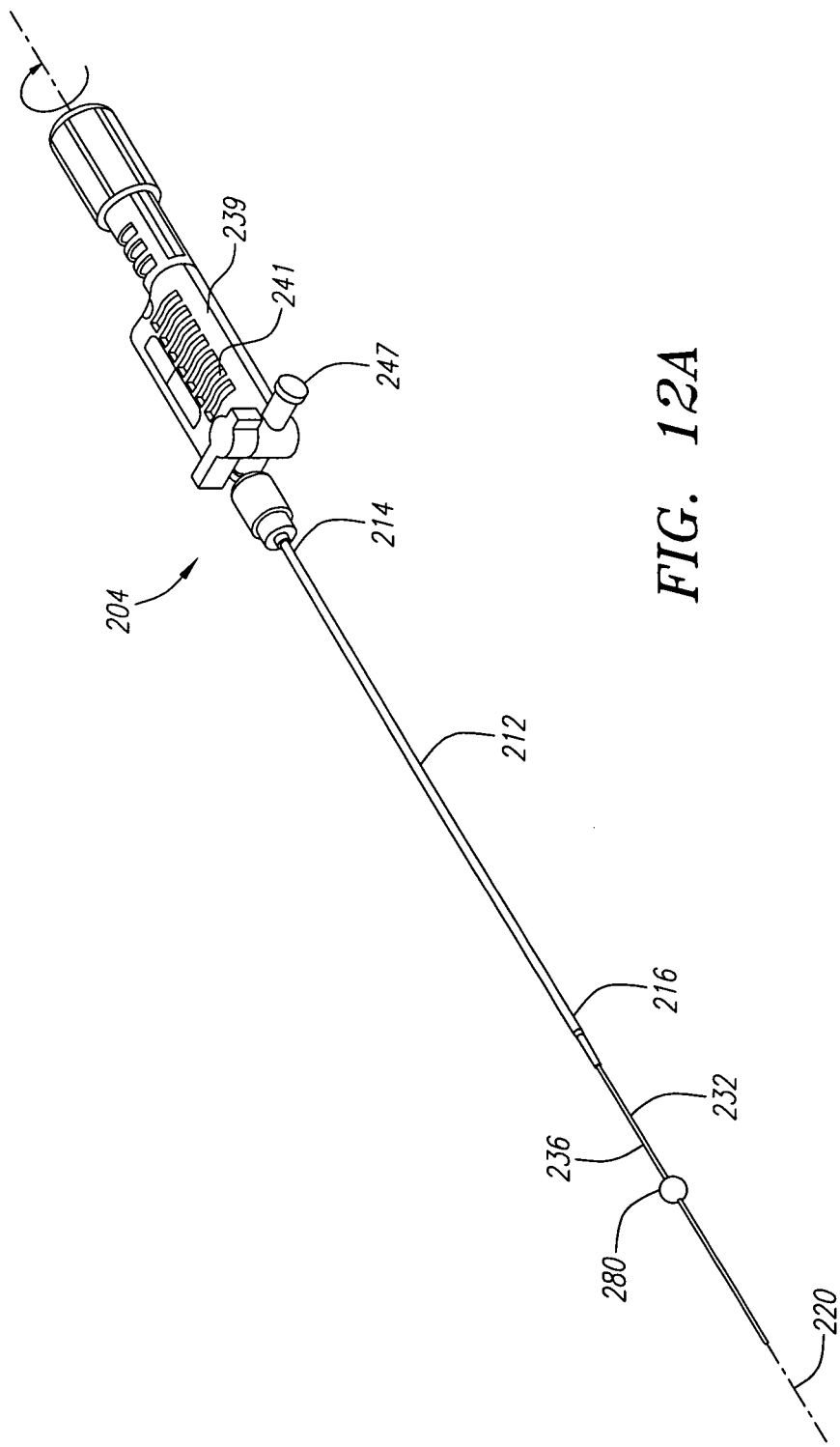
FIG. 12A is a perspective view of an alternative embodiment of an occlusion member, including an actuator switch for expanding and/or collapsing a balloon thereon.
Figure 12B:
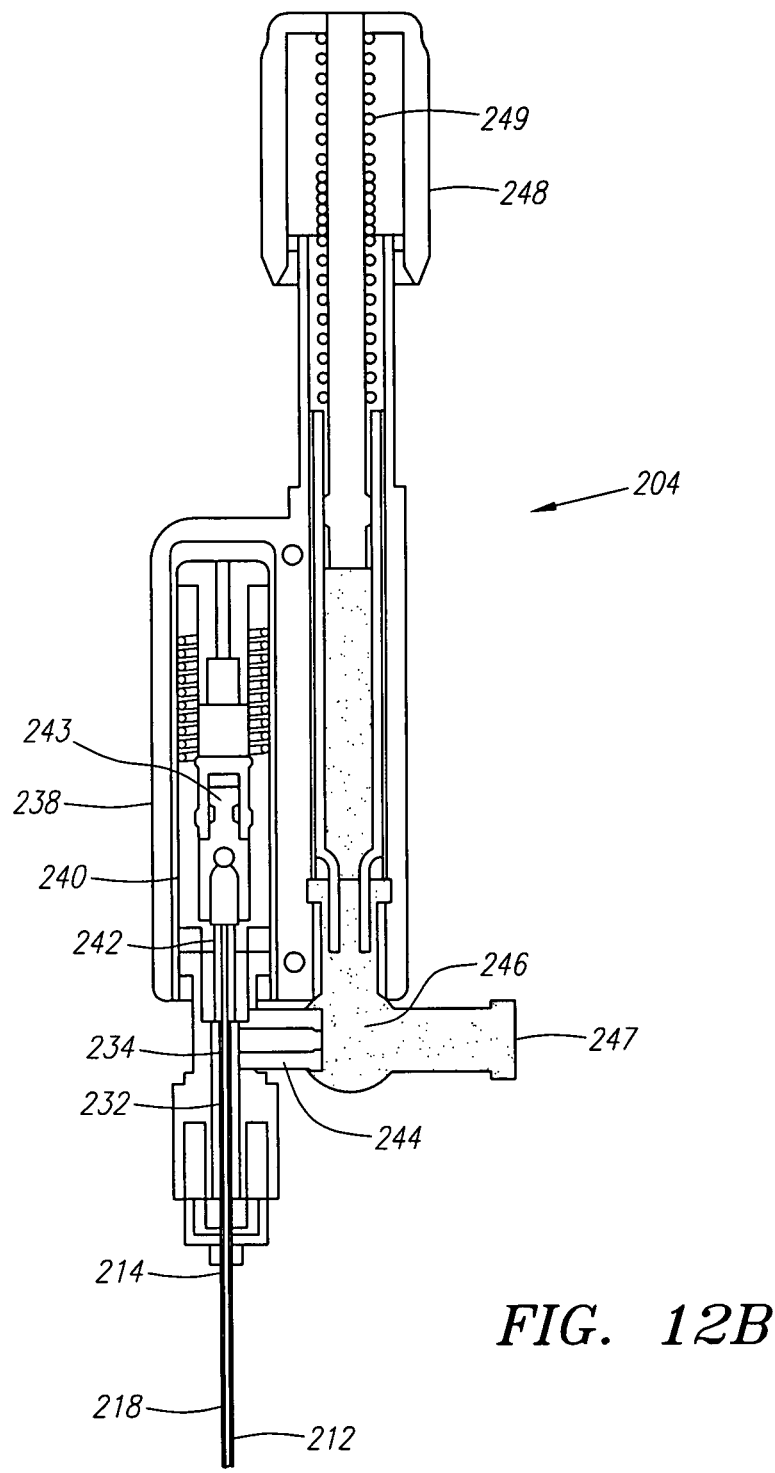
FIG. 12B is a cross-sectional view of the occlusion member actuator switch of FIG. 12A.
Figure 12C:
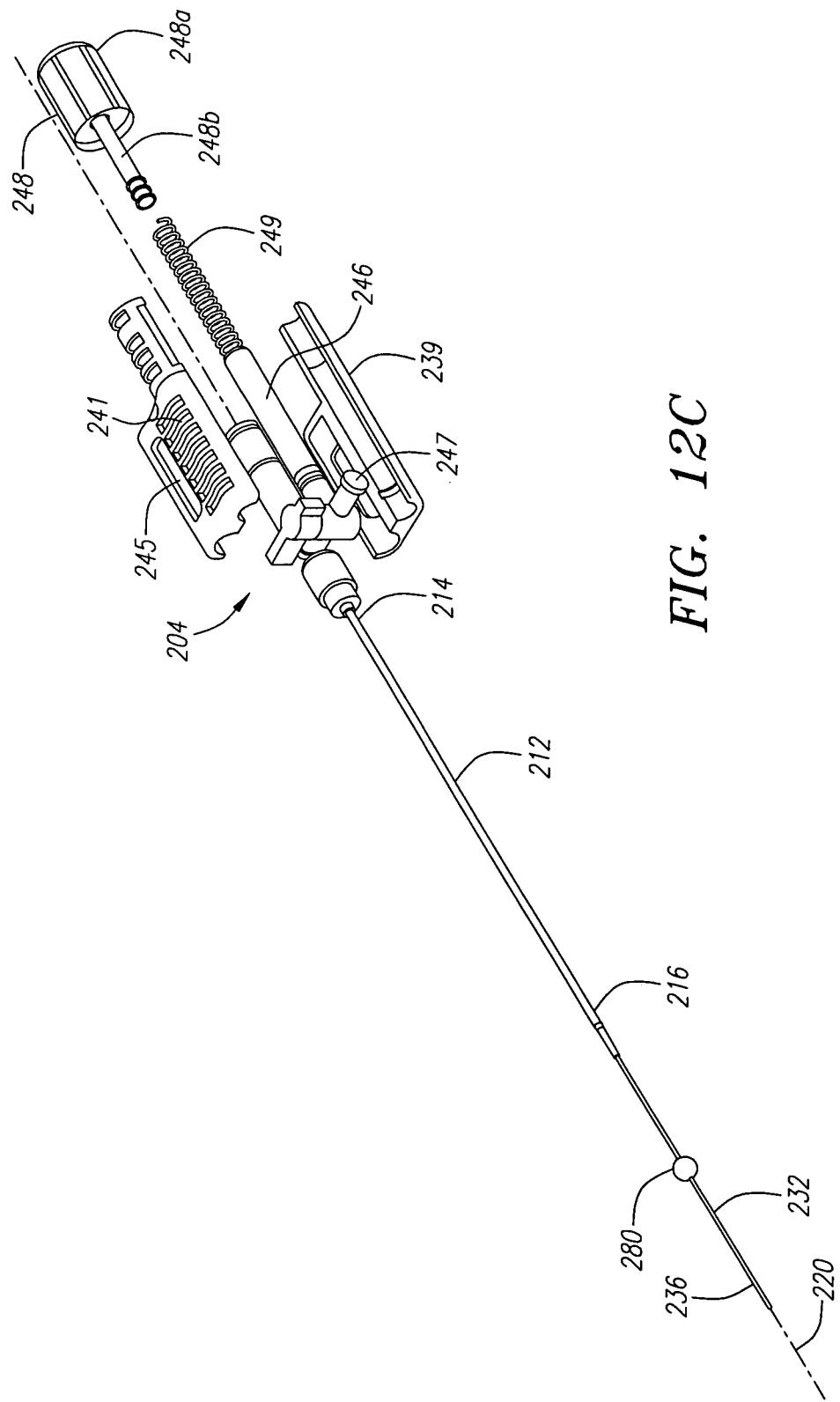
FIG. 12C is an exploded perspective view of the occlusion member of FIG. 12A.

Turning to FIGS. 12A-12C, another embodiment of an occlusion member 204 is shown. Similar to the previous embodiments, the occlusion member 204 includes an outer member 212, an inner member 232 slidably coupled to the outer member 212, a hub subassembly 238 (shown in FIG. 12B) for biasing the inner member 232 relative to the outer member 212, and a balloon or other expandable member 280 (shown expanded in FIGS. 12A and 12C) coupled to the inner and outer members 232, 212. Unlike the previous embodiments, the hub subassembly 238 is self-contained, rather than requiring a syringe or other source of inflation media for expanding the balloon 280, e.g., to improve ease of use and/or allow single user operability.

The outer member 212 may be an elongate tubular body including a proximal end 214, a distal end 216, and a lumen 218 extending between the proximal and distal ends 214, 216, thereby defining a longitudinal axis 220. The inner member 232 may be an elongate wire or other body including a proximal end 234 and a distal end 236. As best seen in FIG. 12B, the inner member 232 is slidably received within the lumen 218 of the outer member 212 such that the distal end 236 of the inner member 232 extends beyond the distal end 216 of the outer member 212. The balloon 280 is coupled to the distal ends 216, 236 of the outer and inner members 212, 232 such that an interior of the balloon 280 communicates with the lumen 218 of the outer member 212, similar to the embodiments described above.

Preferably, the inner member 232 is biased to move distally relative to the outer member 212, i.e., from a proximal position to a distal position (similar to the arrangement shown in FIGS. 3A and 3B, e.g., to facilitate collapsing the balloon 280). For example, the hub subassembly 238 may bias the inner member 232 relative to the outer member 212, similar to the previous embodiments. Generally, as shown in FIG. 12B, the hub subassembly 238 includes a housing 240 extending proximally from the proximal end 214 of the outer member 212 and a piston 243 coupled to the proximal end 234 of the inner member 232. In one embodiment, the piston 243 is biased distally within a chamber 242 of the housing 240 by a spring 274.

The housing 240 also includes an actuator, such as a depression switch 248, and a passage 244 connecting the chamber 242 with a reservoir 246. The switch 248 may include a handle or button 248a and a piston 248b extending from the handle 248a into the reservoir 246. The reservoir 246 may be filled with fluid, thereby allowing fluid to flow into and out of the chamber 242 and the lumen 218 of the outer member 212. For example, the reservoir 246 may be filled via valve 247 from a syringe or other source of inflation media (not shown), similar to the embodiments described above, to cause the balloon 280 to expand and collapse when the switch 247 is activated and deactivated, respectively. Preferably, the reservoir 246 is filled sufficiently with the piston 243 in its distal position and the balloon 280 collapsed without causing the piston 243 to move distally and/or the balloon 280 to expand.

Thereafter, during use, when it is desired to expand the balloon 280, the switch 248 may be depressed to direct the piston 248b into the reservoir 246 to force fluid from the reservoir 246 into the chamber 242 and lumen 218, thereby directing the piston 243 proximally as the balloon 280 expands, similar to the previous embodiments. In a preferred embodiment, the switch 248 is a depression switch that may be depressed distally to expand the balloon 280. When the switch 248 is depressed again, a spring 249 coupled to the switch 248, e.g., surrounding the piston 248a, may direct the switch 248 proximally to its original position, thereby drawing fluid back into the reservoir 246 from the chamber 242 and lumen 218, and collapsing and extending the balloon 280 as the piston 243 moves distally.

Alternatively, other switches, e.g., rotation switches and the like (not shown), may be provided instead of the depression switch 248. In addition or alternatively, other piston/spring arrangements may be provided in the housing 240, similar to the previous embodiments.

In addition, the occlusion member 204 may include a cover 239 for concealing and/or protecting the internal components of the housing 240, actuator, etc. As described more particularly below, the cover 239 may include sets of grooves for connecting the occlusion member 204 to a tensioner, such as that shown in FIG. 13. Optionally, a window 245 may be provided in the cover 239 for observing the piston 243 within the housing 240. For example, the window or cover may include graduated markings (not shown) indicating a pressure level, and the piston 243 may include a visual marker (also not shown). As the piston 243 slides within the housing 240, the visual marker on the piston 243 may align with the graduated markings along the window 245, thereby indicating the pressure within the housing 240. This may facilitate initially filling the reservoir 246 during set-up. In addition or alternatively, if a switch having multiple positions is provided, the graduated markings may indicate the position of the piston and the internal pressure as the switch is ratcheted through the multiple positions.

Returning again to FIG. 1, the delivery device 8 may include a dual syringe assembly 130 that includes two components of a sealing compound, a "Y" fitting 140, and a static mixer 110. The syringe assembly 130 may include a pair of syringe barrels 132 including access ports or outlets 136 and a plunger assembly 133 slidable into the barrels 132 to cause the components therein to be delivered through the outlets 136. In one embodiment, the plunger assembly 133 includes a pair of plungers 134 that are coupled to one another yet are received in respective barrels 132. Thus, both plungers 134 may be manually depressed substantially simultaneously to deliver the components in the syringe barrels 132 out together.

The plunger assembly 133 may also include a trigger that may actuate the retraction assembly 10, as described further below. For example, as shown in FIG. 1, the trigger may be a shaft or piston 135 that extends distally between the plungers 134. Thus, when the plungers 134 are inserted into the barrels 132, the shaft 135 may extend distally between the barrels 132.

The "Y" fitting 140 may include proximal sections 142 that communicate with a single distal section 144. Thus, the "Y" fitting 140 may be connectable to outlets 136 of the syringes 132 such that the components ejected out of the syringes 132 may mix before being delivered into the side port 102 of the introducer sheath assembly 6. The proximal and distal sections 142, 144 may include connectors, e.g., luer lock connectors and the like (not shown), for connecting with outlets 136 of the syringes 132 and/or with the mixer 110, the tubing 106, and/or the side port 102 of the introducer sheath assembly 6. The "Y" fitting 140 may have a variety of shapes, depending upon the performances properties and/or manufacturing parameters, and should not be restricted to a particular shape, such as a true "Y" shape, but may still be referred to as a "Y" fitting.

The mixer 110 may be a tubular body including vanes or other internal structures (not shown) that enhance the components mixing thoroughly together as they pass therethrough. Similar to the "Y" fitting 140, the mixer 110 may include connectors (not shown) for releasably or substantially permanently connecting the mixer 110 to the "Y" fitting 140, tubing 106, and the like.

In one embodiment, a liquid precursor polymer compound is provided in each syringe barrel 132 of the syringe assembly 130 that, when mixed together, may be activated to form a hydrogel. Additional information on hydrogels and systems for delivering them are disclosed in U.S. Pat. Nos. 6,152,943, 6,165,201, 6,179,862, 6,514,534, and 6,379,373, and in copending application Ser. No. 09/776,120 filed Feb. 2, 2001, Ser. No. 10/010,715 filed Nov. 9, 2001, and Ser. No. 10/068,807 filed Feb. 5, 2002. The disclosures of these references and any others cited therein are expressly incorporated by reference herein.

Optionally, the syringe assembly 130 may include one or more valves coupled to the outlets 136 of the syringes 132. For example, a valve may be used to connect the syringe barrels 132 to a source of sealing components for introducing the components into the syringe barrels 132 during set-up before sealing a puncture created during a procedure. Once the syringe barrels 132 are loaded, the valve may be closed to substantially seal the outlets 136, e.g., to temporarily store the components during a procedure. Finally, the valve may be used to connect the syringes 132 to the "Y" fitting 140 or other delivery line to allow the components to be delivered into a puncture.

Figure 15:
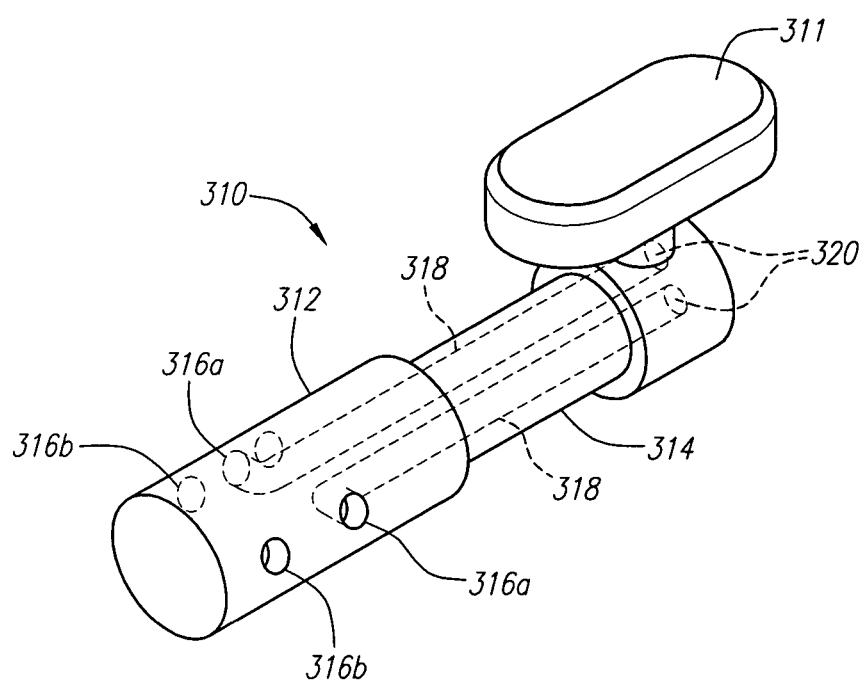
FIG. 15 is a perspective view of a linear valve.

As shown in FIGS. 15, 16A, and 16B, an embodiment of a linear valve 310 is shown that may be incorporated into a delivery device 308. As best seen in FIG. 15, the valve 310 generally includes a piston or other member 314 slidable within a housing 312. The housing 312 includes two sets of side ports 316a, 316b that may be aligned with lumens 318 extending through the piston 314 when the piston 314 is in first and second positions, respectively. The lumens 318 may be coupled to the outlets of respective syringe barrels of a syringe assembly (not shown) at end ports 320.

As best seen in FIGS. 16A and 16B, the linear valve 310 may be coupled to the delivery device 308, e.g., by tubing 324. For example, outlets 336 of syringe barrels 332 may be coupled to the end ports 320 (shown in FIG. 15) by tubing 324c. The first set of side ports 316a may be connected to a source of sealing components, such as vials 322 (not shown), by tubing 324a. The second set of ports 316b may be coupled to inlets 432 of a "Y" fitting 339 by tubing 324b.

During use, the valve 310 may be placed in the first position shown in FIG. 16A, e.g., by directing actuator button 350 proximally. Sealing compound, e.g., precursor polymer components, may then be loaded, mixed, and/or reconstituted from the vials 322 into respective syringe barrels 332 via the tubing 324a, side ports 316a, lumens 318, end ports 320, and tubing 324c. For example, in one embodiment, the syringe barrels 332 may include liquid solvent and/or buffer solution, and the vials 322 may include precursor polymer components in powder or other solid form. With the valve in the first position, the plunger assembly 333 may be depressed, delivering the liquid buffer solution through the valve 310 into the vials 322.

The valve 310 may then be moved to a closed position, e.g., an intermediate position such that the lumens 318 do not communicate with either of the sets of side ports 316a, 316b. The vials 322 (e.g., along with the entire delivery device 308) may then be shaken to mix and/or reconstitute the precursor polymer compounds into liquid form. The valve 310 may then be returned to the first position, and the plunger assembly 133 may be withdrawn from the syringe barrels 332 in order to draw a desired amount of the reconstituted precursor components into the barrels 332. For example, the barrels 332 may be loaded only with a predetermined amount of the components based upon an approximation of the volume to be delivered into a puncture being sealed. The barrels 332 may include volumetric graduation indicators that may guide a user to draw the predetermined amount of sealing components into the barrels 332.

When it is time to deliver the sealing components, the valve 310 may be placed in the second position shown in FIG. 16B, e.g., by directing the actuator button 350 distally. In this position, the outlets 336 of the syringes 332 communicate with the "Y" fitting 340, allowing the sealing compound to be delivered via the tubing 324c, end ports 320, lumens 318, side ports 316b, and tubing 324b. The "Y" fitting 230 may coupled to a delivery line (not shown), as described elsewhere herein for delivering the sealing compound into a puncture.

It will be appreciated that the valve 310 may facilitate a user filling the syringes 332 with a desired volume of sealing compound from a vial 322 or other source with the valve 310 in a loading position, including allowing mixing and/or reconstituting sealing components. During use, the valve 310 may simply be moved to a delivery position to allow the sealing compound to be delivered. In addition, if desired, the valve 310 may have a third position where the lumens 318 do not communicate with either of the side ports 316a, 316b, thereby substantially eliminating the risk of precursor polymer materials escaping from the syringes 332 and/or mixing prematurely.

Such a valve 310 may be convenient to use for a manually infected system, such as those described above. In addition or alternatively, such valves may be particularly convenient for an auto-injector system, i.e., a system that automatically delivers a sealing compound once the system is triggered or otherwise activated, as described further below.

Figure 17A:
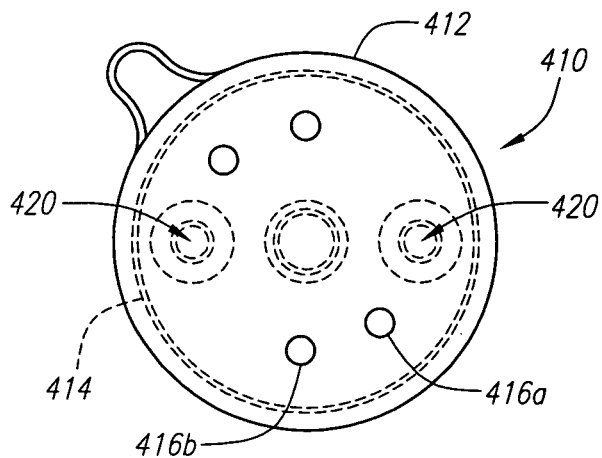
FIGS. 17A-17C are end views of a revolver valve that may be connected to a syringe assembly, rotated into three different positions.
Figure 17B:
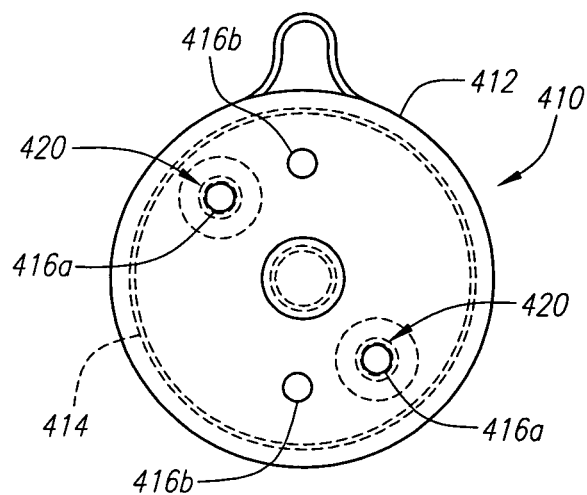
Figure 17C:
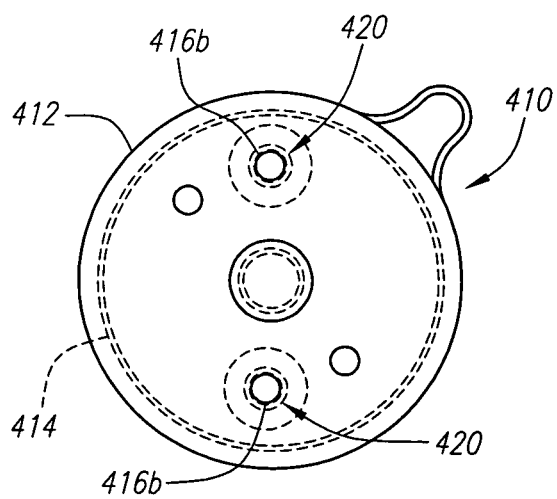

It will be appreciated that other valve configurations may be provided instead of the linear valve and tubing arrangement shown in FIGS. 15, 16A, and 16B, such as a stopcock or rotating valve. For example, FIGS. 17A-17C show an embodiment of a revolver valve 410 that may be provided, including a valve body 414 (shown in phantom) rotatable within a housing 412. The valve 410 includes ports 420 (shown in phantom) that may be connected to syringes of a delivery device (not shown), and first and second sets of ports 416a, 416b that may be connected to respective vials and a "Y" fitting (also not shown), respectively, e.g., by tubing (not shown), similar to the previous embodiment.

Internal lumens or passages (not shown) in the body 414 communicate with the ports 420 and may selectively communicate with the ports 416a or 416b, depending upon the position of the body 414 relative to the housing 412. For example, with the body 414 in the first position shown in FIG. 17A, the ports 420 do not communicate with either of the other ports 416a, 416b, and the valve 410 is closed or off. When the body 414 is rotated to the second position shown in FIG. 17B, the ports 420 communicate with the ports 416a, allowing syringes to be filled from vials, as described above. Finally, when the body 414 is rotated to the third position shown in FIG. 17C, the ports 420 communicate with the ports 416b, creating a passage through which the precursor polymers may be injected from syringes through a "Y" fitting and into a patient (not shown), as described above.

Figure 9:
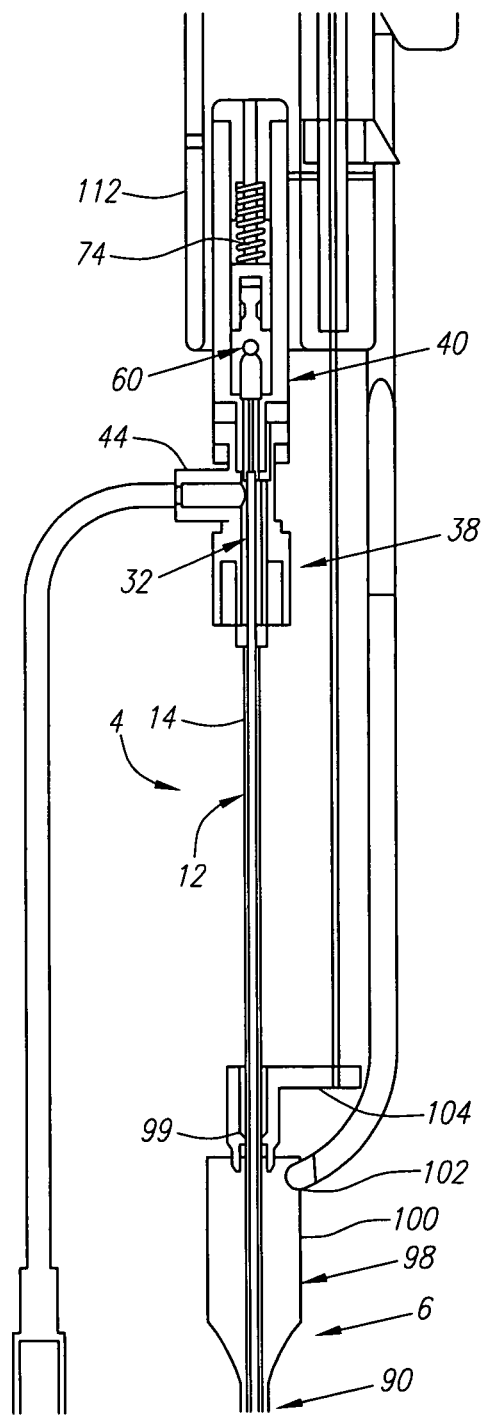
FIG. 9 is a cross-sectional view of the occlusion member, the introducer sheath assembly, and the retraction assembly of FIG. 1.

Turning to FIGS. 1 and 9, an embodiment of a retraction assembly 10 is shown that generally includes a housing 112 to which the occlusion member 4 may be secured, a shaft 114 slidably coupled to the housing 112 and the introducer sheath assembly 6, and a lock/release mechanism 116 for controlling movement of the shaft 114 relative to the housing 112. The housing 112 may include one or more connectors (not shown) for securing the occlusion member 4 to the housing 112. For example, the housing 112 may include a recess for receiving the hub subassembly 38 of the occlusion member 4 therein and/or one or more catches, detents, and the like (not shown) for releasably or substantially permanently securing the occlusion member 4 thereto. Alternatively, the occlusion member 4 may be incorporated into or otherwise substantially permanently attached to the retraction assembly 10.

The introducer sheath assembly 6 may be slidably disposed over the occlusion member 4 before or after the occlusion member 4 is secured to the retraction assembly 10. For example, the occlusion member 4 may be mounted to the retraction assembly 10 during manufacturing such that the shaft 114 extends distally adjacent to the outer member 12 of the occlusion member 4. The shaft 114 and the introducer sheath assembly 6 may include one or more connectors for releasably or substantially permanently connecting the shaft 114 to the introducer sheath assembly 6.

For example, a distal end 121 of the shaft 114 may include a hook, tab, or other element (not shown) that may be received in a hole or pocket (also not shown) in the flange 104 on the introducer sheath assembly 6. During a procedure, as described further below, the balloon 80 of the occlusion member 4 may be inserted into the housing 98 and advanced distally through the lumen 96 of the introducer sheath 90 until the balloon 80 extends beyond the distal end 94 of the introducer sheath 90. The distal end 121 of the shaft 114 may then be attached to the flange 104. Once the shaft 114 is attached to the flange 104, axial movement of the introducer sheath assembly 6 may be coupled to axial movement of the shaft 114.

Optionally, the apparatus 2 may include a cover (not shown) for concealing the various components of the retraction assembly 10, along with the components of the occlusion member 4 and/or introducer sheath assembly 6 to which users do not need access.

Figure 10B:
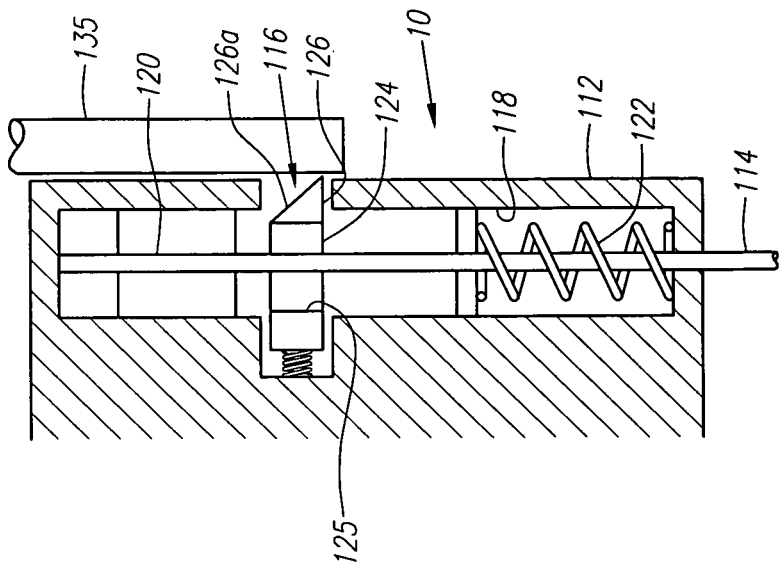
FIGS. 10A and 10B are cross-sectional details of a lock mechanism of the retraction assembly of FIG. 1 in outward locked and inward actuated positions, respectively.
Figure 10A:
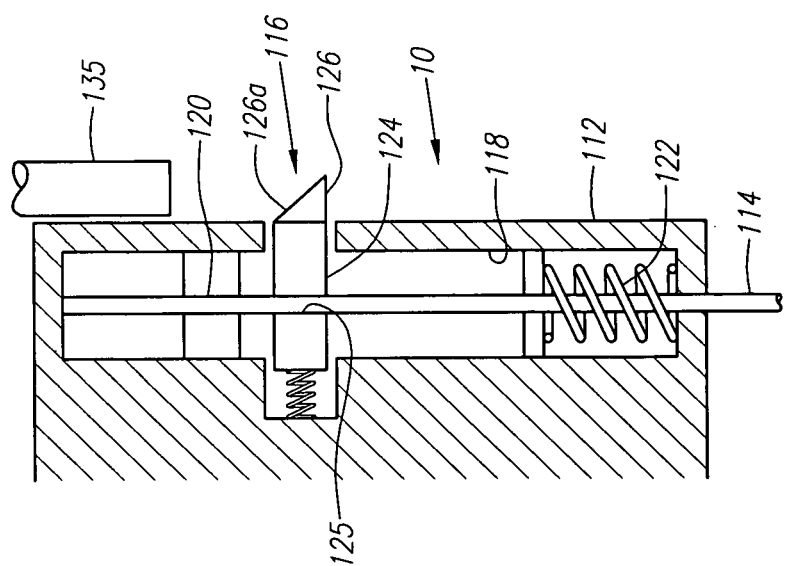

With additional reference to FIGS. 10A and 10B, the housing 112 of the retraction assembly 10 may include a passage 118 therein that extends substantially parallel to the longitudinal axis 20. A proximal end 120 of the shaft 114 may be slidably received in the passage 118, while the distal end 121 of the shaft 114 may be coupled to the introducer sheath assembly 6, e.g., to the flange 106, as described above. The shaft 114 may be biased to move within the passage 118 to bias axial movement of the introducer sheath 90 coupled to the retraction assembly 10. For example, a compression spring 122 or other element may be provided in the passage 118 for biasing the shaft 114 proximally relative to the housing 112.

The lock/release mechanism 116 may include a lock member 124 that is disposed within the housing 112 and that is movable transversely relative to the passage 118. A spring or other mechanism (not shown) may be provided for biasing the lock member 124 outwardly such that a release button 126 of the lock member 124 extends through an opening 128 in the housing 112. The release button 126 may include a sloped outer proximal surface 126a, e.g., to convert an axial force from the piston 135 of the plunger assembly 130 into a transverse force for moving the lock member 124 inwardly.

The lock member 124 may include connectors for releasably securing the shaft 114 at one or more positions within the passage 118. For example, the lock member 124 may include an aperture 125 through which a portion of the shaft 114 may extend. When the shaft 114 is in a distal position and the lock member 124 is in an outer locked position (shown in FIG. 10A), the lock member 124 may engage the shaft 114 to prevent the shaft 114 from moving axially within the passage 118. For example, a portion of the lock member 124 may simply frictionally engage the shaft 114. Alternatively, the lock member 124 and shaft 114 may include one or more cooperating detents (not shown) that engage one another when the lock member 124 is in the outer locked position.

When the lock member 124 is pushed inwardly, e.g., when the release button 126 is depressed (shown in FIG. 10B), the shaft 114 may be released from the lock member 124 and free to move axially within the passage 118. Because of the bias provided by the spring 122, the shaft 114 may move proximally within the passage 118 until the proximal end 116 of the shaft 114 reaches the end of the passage 118 or encounters a stop (not shown), preventing further proximal movement.

Because the shaft 114 is coupled to the introducer sheath assembly 6 (not shown, see FIGS. 1 and 9), when the shaft 114 is locked in the distal position, the introducer sheath 90 may be secured relative to the outer member 12. For example, in the distal position, the distal end 94 of the introducer sheath 90 may be located a predetermined distance proximal to the balloon 80 of the occlusion member 4, as shown in FIG. 1. Once the shaft 114 is released and moves proximally, the introducer sheath 90 is directed proximally, thereby moving the distal end 94 of the introducer sheath 90 away from the balloon 80 of the occlusion member 4 (not shown). As explained further below, the distance that the introducer sheath 90 is moved by the shaft 114 preferably corresponds generally to the length of a puncture or other tract through tissue that is being sealed by the apparatus 2.

Returning to FIG. 1, the lock member 124 is preferably released automatically as sealing compound is being delivered from the delivery device 8. To accomplish this, in the embodiment shown, the delivery device 8 includes piston 135 extending from the plunger assembly 133. As can be seen in FIG. 1, the piston 135 is preferably aligned axially with the release button 126 extending from the housing 112 of the retraction assembly 10. Thus, when a user depresses the plunger assembly 133, the piston 135 may contact the sloped proximal surface 126a of the release button 126. As the plunger assembly 133 is depressed further, as shown in FIG. 10B, the piston 135 may bear against the sloped proximal surface 126a, thereby directing the release button 126 and, consequently, the lock member 124 inwardly to release the shaft 114.

Preferably, the distance between the piston 135 and the release button 126 is predetermined such that the lock member 124 is released at a desired time during the stroke of the plunger assembly 133. For example, as explained further below, as the plunger assembly 135 is depressed, the components in the syringe barrels 132 may be injected through the "Y" fitting 140, into the housing 98 of the introducer sheath assembly 6, and through the lumen 96 of the introducer sheath 90. Once the mixed sealing material begins to exit the distal end 94 of the introducer sheath 90, the lock member 124 may be released to allow the introducer sheath 90 to retract proximally, thereby filling a puncture within which the introducer sheath 90 is disposed with the sealing material.

Figure 18A:
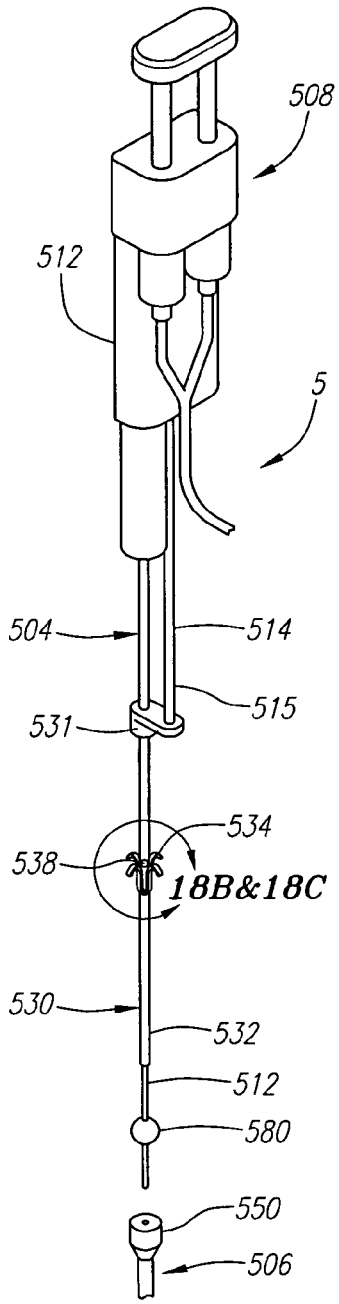
FIG. 18A is a perspective view of another embodiment of an apparatus for sealing a puncture through tissue, including a retraction assembly, an introducer sheath, and an occlusion member.
Figure 18B:
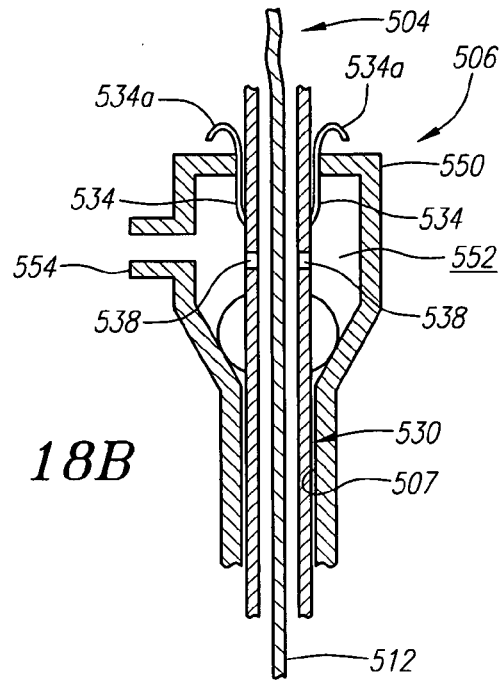
FIGS. 18B and 18C are cross-sectional details of the apparatus of FIG. 18A.
Figure 18C:
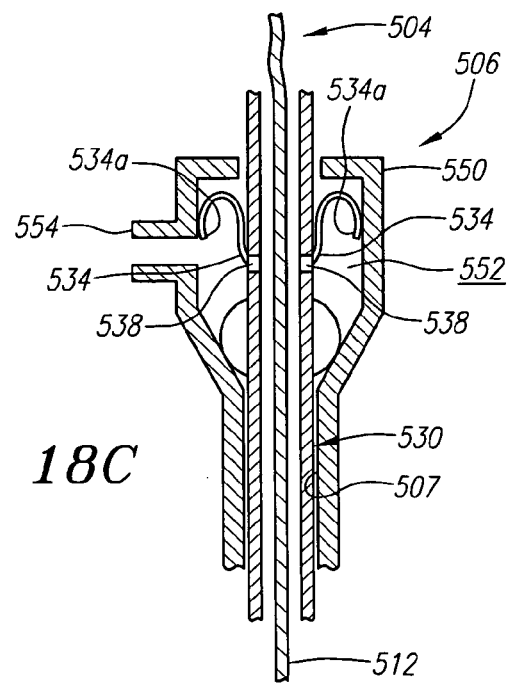

Turning to FIG. 18A-18C, another embodiment is shown of an apparatus 502 that includes an occlusion member 504, an introducer sheath 506, a delivery device 508, and a retraction assembly 510. The occlusion member 504 may be releasably or substantially permanently attached to the retraction assembly 510, similar to the previous embodiments. The introducer sheath 506 may be a conventional introducer sheath or may be similar to other embodiments described herein. The delivery device 508 may be a dual-syringe assembly, including manual injection or automatic injection, also similar to other embodiments described herein.

Similar to the previous embodiments, the retraction assembly 510 may include a housing 512 to which the occlusion member 504 may be secured, a shaft 514 slidably coupled to the housing 512, and a lock/release mechanism (not shown) for controlling movement of the shaft 514 relative to the housing 512, e.g., based upon use of the delivery device 508. Also, similar to the previous embodiments, the occlusion member 504 may include an outer member 512 and a balloon 580 carried on a distal end 516 of the outer member 512. The occlusion member 504 may include one or more of the other components described above with respect to other embodiments.

Unlike the previous embodiments, the retraction assembly 510 includes a delivery sheath 530 that surrounds and is slidable relative to a proximal portion of the outer member 516. The delivery sheath 530 includes a distal end 532 having a size and shape allowing the delivery sheath 530 to be inserted into a lumen 507 of the introducer sheath 506.

The delivery sheath 530 is coupled to the shaft 514 such that axial movement of the delivery sheath 530 corresponds to movement of the shaft 514. For example, a distal end 515 of the shaft 514 and a proximal end 531 of the delivery sheath 530 may include cooperating connectors (not shown) for releasably or substantially permanently coupling the shaft 514 and the delivery sheath 530 to one another, similar to the connectors described above for the shaft 114 and introducer sheath assembly 6 shown in FIG. 1.

The delivery sheath 530 also includes a pair of detents 534 located a predetermined distance from the distal end 532 for coupling the delivery sheath 530 to the introducer sheath 506. In an exemplary embodiment, best seen in FIGS. 18B and 18C, each detent 534 is a strip of spring material, e.g., a pseudoelastic and/or superelastic material, such as stainless steel or Nitinol, that has a fixed end attached to the delivery sheath 530, and a free end 534a formed into a loop. Alternatively, both ends of the detent may be fixed, yet define a loop (not shown). Because of the elasticity of the spring material, the detent 534 may be collapsed against the delivery sheath 530, e.g., if the loop is unrolled or collapsed, yet may resume its looped shape when any external force is removed.

As described above with respect to earlier embodiments, the introducer sheath 506 may include a housing 550 defining a cavity 552 and including a side port 554 communicating with the cavity 552 and, consequently, with the lumen 507 of the introducer sheath 506. The housing 550 may also include one or more seals (not shown) for substantially sealing the cavity 552, yet allowing one or more instruments, e.g., the occlusion member 504 and/or the delivery sheath 530 to be inserted into the lumen 507.

As shown in FIG. 18B, when the delivery sheath 530 is advanced into the introducer sheath 506, the detents 534 may contact the housing 550, causing the free ends 534a to unroll as the detents 534 enter the housing 550. Once the detents 534 are located completely within the cavity 552, the free ends 534a may resume their looped shape. Alternatively, if both ends of the detents are fixed, the detents may simply collapse as they are directed into the housing 550 and then resilient return to their looped shape once located within the cavity 552. Thereafter, if the delivery sheath 530 is directed proximally away from the introducer sheath 506, the detents 534 may contact the wall of the housing 550, preventing the delivery sheath 530 from being removed easily from the introducer sheath 530. Thus, proximal movement of the delivery sheath 530 will cause proximal movement of the introducer sheath 506.

Although a pair of detents 534 are shown opposite one another on the delivery sheath 530, it will be appreciated that one or more detents may be provided at one or more locations around the delivery sheath 530 for coupling to the introducer sheath 506. In addition or alternatively, additional connectors may be provided, such as ramped tabs and the like instead of the spring loops described above.

Optionally, as shown in FIGS. 18B and 18C, the delivery sheath 530 may also include an annular seal 536 adjacent to, and preferably, distal to the detents 534. The seal 536 may be a solid mass of resilient material, e.g., plastic, foam rubber, and the like, e.g., formed into a tapered wedge shape contoured to provide sufficient interference with the interior of the housing 550. Alternatively, the seal 536 may be a balloon or other membrane that may be filled with a desired volume of fluid, e.g., saline, nitrogen, carbon dioxide, and the like. When the delivery sheath 530 is inserted into the introducer sheath 506, the seal 536 may compress sufficiently to allow the seal 536 to enter the cavity 552. As the delivery sheath 530 is advanced to engage the detents 534 within the housing 550, the seal 536 may substantially engage an interior of the housing 550 and/or introducer sheath 506. Thus, the seal 536 may substantially seal the lumen 507 of the introducer sheath 506 from fluid flow distally between the delivery sheath 530 and the introducer sheath 506. One advantage of such a seal 536 is that it may allow a delivery sheath 530 having a fixed size to be inserted into a variety of sized introducer sheaths, while still substantially sealing the lumen of the introducer sheaths.

In the embodiment shown in FIGS. 18B and 18C, the delivery sheath 530 may include one or more openings 538 (a pair being shown) adjacent the detents 534 and communicating with a lumen 540 extending to the distal end 532 of the sheath 530. In this embodiment, the delivery sheath 530 may have sufficient length such that, when the delivery sheath 530 is fully received in the introducer sheath 506, the distal end 532 may extend beyond the distal end (not shown) of the introducer sheath 506. Sealing compound may be injected into the side port 554 of the housing 550 using any of the delivery devices described herein. With the lumen 507 of the introducer sheath 506 sealed by the seal 536, the injected sealing compound may be forced through the openings 538 into the lumen 540 and out the distal end 532 of the delivery sheath 530.

Optionally, the delivery sheath 530 and the occlusion member 4 may include cooperating detents, connectors, or other features (not shown) for limiting distal movement of the delivery sheath 530 relative to the occlusion member 4. For example, the delivery sheath 530 may be movable distally until the cooperating features contact one another, e.g., such that the distal end 532 of the delivery sheath 530 is located a minimum distance from the balloon 80 of the occlusion member 4, e.g., at least about five millimeters (5 mm). Such features may prevent the delivery sheath 530 from being directed against or too close to the balloon 80, which may increase the risk of sealing material being delivered into the vessel (not shown), as explained further below.

Alternatively, if the seal 536 and openings 538 are eliminated from the delivery sheath 530, the length of the delivery sheath 530 may be reduced to have a relatively short length compared to the introducer sheath 506, e.g., sufficient to engage the detents 534 within the housing 550. In this alternative, when sealing compound is injected into the side port 554, the sealing compound may pass along the lumen 507 of the introducer sheath 506 and out its distal end (not shown). Thus, a shortened delivery sheath may simply be a connector for coupling movement of the introducer sheath 506 to the retraction assembly 510.

In a further alternative, a sheath, similar to the delivery sheath 530 described above, may be utilized in an embodiment without a retraction assembly. In such an embodiment, the delivery sheath may include an enlarged handle on its proximal end to facilitate manual manipulation of the delivery sheath once it is coupled to the introducer sheath. For example, the delivery sheath may be inserted into the introducer sheath until the detents enter the housing of the introducer sheath, thereby coupling subsequent movement of the introducer sheath to the delivery sheath.

Optionally, the delivery sheath may include a seal in its proximal end, allowing an occlusion member to be inserted into the delivery sheath, and consequently, through the introducer sheath, using the methods described elsewhere herein. Thus, the delivery sheath may be drawn proximally while sealing compound is being delivered through the introducer sheath, thereby manually retracting the introducer sheath and at least partially filling a puncture with sealing compound.

Turning to FIGS. 11A-11F, an exemplary method for sealing a passage through tissue is shown using an apparatus similar to that shown in FIG. 1. In the shown embodiment, the passage is a percutaneous puncture 190 extending from a patient's skin 192 to a blood vessel or other body lumen 194. For example, the vessel 194 may be a peripheral artery, e.g., a femoral artery, a carotid artery, and the like. It will be appreciated that the apparatus and methods in accordance with the various embodiments of the present invention may be used to seal other passages within a patient's body.

Figure 11A:
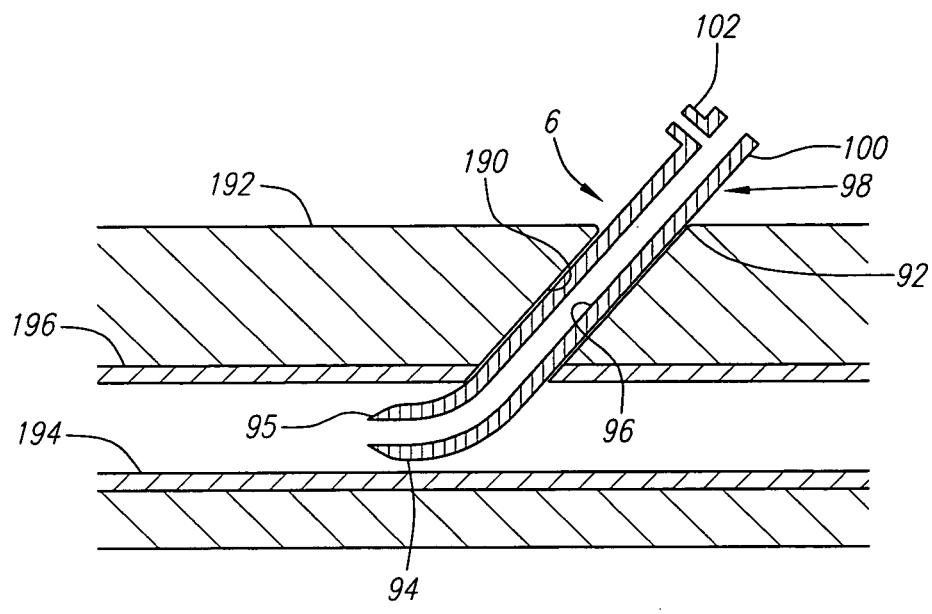
FIGS. 11A-11F are cross-sectional views of a percutaneous puncture communicating with a blood vessel showing a method for sealing the puncture, in accordance with the present invention.

Initially, as shown in FIG. 11A, the introducer sheath 90 of the introducer sheath assembly 6 may be placed within the puncture 190 such that the distal end 94 is disposed within the vessel 192 without the other components of the apparatus 2. The introducer sheath 90 may be introduced within the puncture 190 using conventional methods, such as those used to insert known introducer sheaths. Alternatively, a separate introducer sheath (not shown) may be inserted into the puncture 190 using known procedures.

One or more instruments (not shown) may be advanced through the introducer sheath 90 (or separate introducer sheath) and into the vessel 194, e.g., to perform one or more diagnostic and/or therapeutic procedures within the patient's body. The one or more instruments may include catheters, e.g., balloon catheters, stent delivery catheters, imaging catheters, and the like, guidewires, and/or other devices. Upon completing the procedure(s), any instruments may be removed and the puncture 190 may be sealed using an apparatus, such as that shown in FIGS. 1-6 and described above.

Figure 11B:
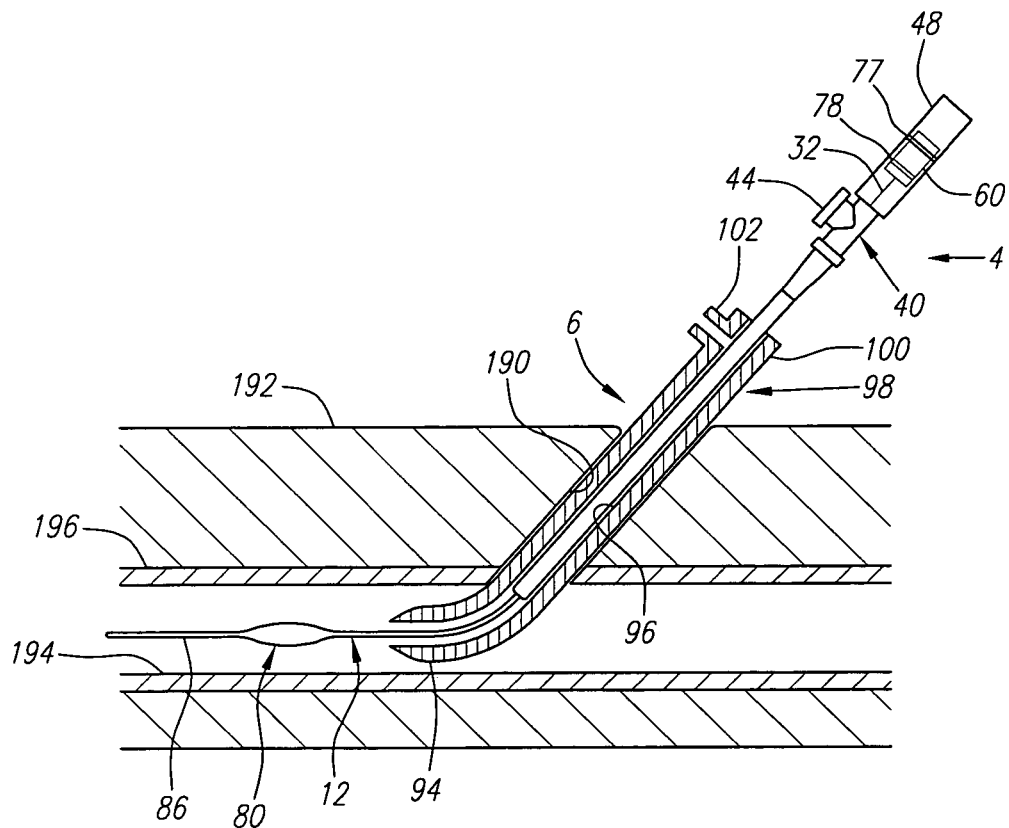

Turning to FIG. 11B, with the balloon 80 in the collapsed state, the occlusion member 4 may be inserted through the lumen 96 of the introducer sheath 90 until the balloon 80 is disposed within the vessel 194. Once the occlusion member 4 is inserted sufficient distance, the retraction assembly 10 may be coupled to the introducer sheath assembly 6. For example, the shaft 114 may include a hook or other connector (not shown) that may be easily coupled to the flange 104 of the introducer sheath assembly 6, as described above. Alternatively, if a separate introducer sheath is provided, this introducer sheath may be removed, and the apparatus 2, preassembled by the manufacturer or by the user before use (e.g., such that the introducer sheath assembly 6 is disposed over the occlusion member 4 and is coupled to the retraction assembly 10), may be inserted into the puncture 190. In a further alternative, a retraction assembly with a delivery sheath surrounding the occlusion member (not shown) may be coupled to the introducer sheath 90 by coupling the delivery sheath to the introducer sheath 90, as described above.

With the balloon 80 collapsed, the occlusion member 4 may be inserted through the introducer sheath 90 into the puncture 190, e.g., freely or over a guidewire (not shown), until the balloon 80 exits the distal end 94 of the introducer sheath 90 and is advanced into the puncture 190. Optionally, the apparatus 2 may include one or more markers, e.g., radiopaque markers (not shown) on the outer member 12 of the occlusion member 4 and/or on the introducer sheath 90, to facilitate monitoring insertion of the apparatus 2 using external imaging, e.g., fluoroscopy, ultrasound, magnetic resonance imaging ("MRI"), and the like. Alternatively or in addition, one or more visual markers (not shown) may be provided, e.g., on the proximal end 14 of the outer member 12 and/or the introducer sheath 90.

Figure 11C:
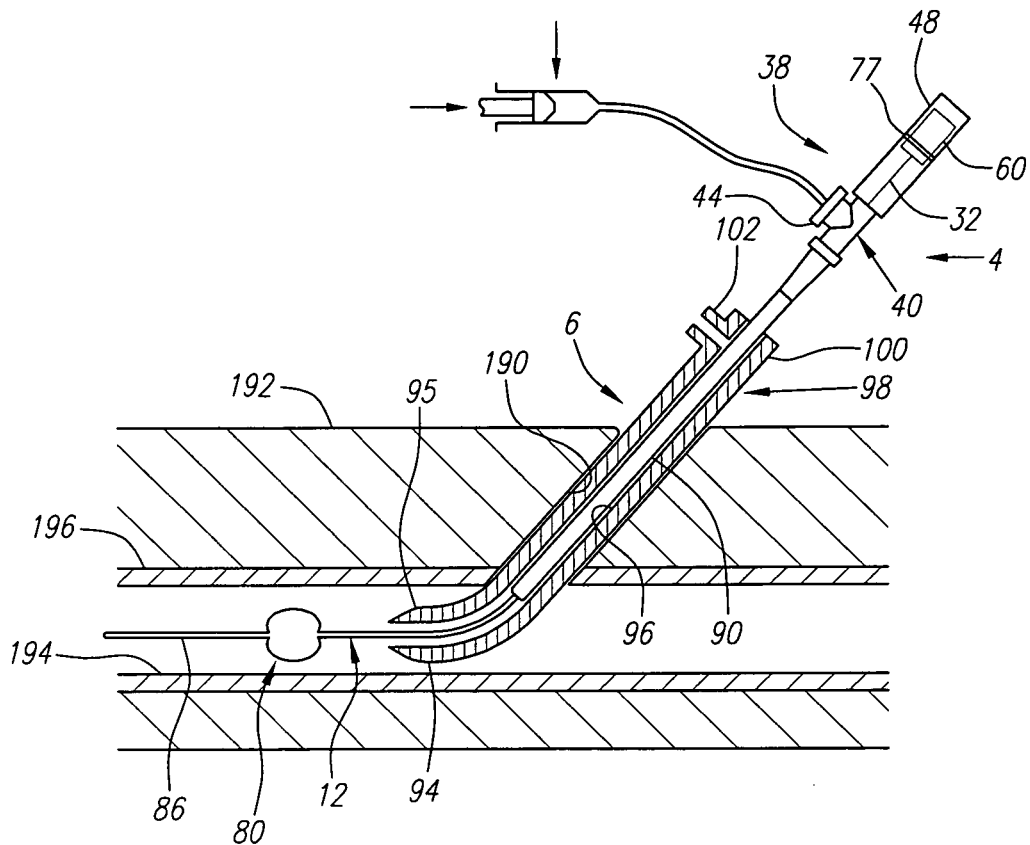

As shown in FIG. 11C, once the balloon 80 is disposed within the vessel 194, the balloon 80 may be expanded to the expanded state. For example, fluid may be introduced into the side port 44 from a syringe 160 through the outer member 12 and into the balloon 80. As explained above, as fluid is introduced into the side port 44, the inner member 32 may be moved proximally relative to the outer member 12, thereby causing the balloon 80 to shorten as it expands. Preferably, the fluid is introduced until the piston 60 moves proximally and markers 77, 78 are aligned with one another, as shown in FIG. 11C, to inform the user that a desired pressure has been reached and/or that the balloon 80 has been expanded to a desired size. Alternatively, the occlusion member 4 may include a pressure gauge or other indicator (not shown) that may provide the user visual confirmation that the balloon 80 has been expanded to a desired size and/or configuration. Alternatively, the occlusion member may include a reservoir of fluid that is delivered into the balloon 80 when an actuator is activated, as described elsewhere herein with respect to FIGS. 12A-12C.

Figure 11D:
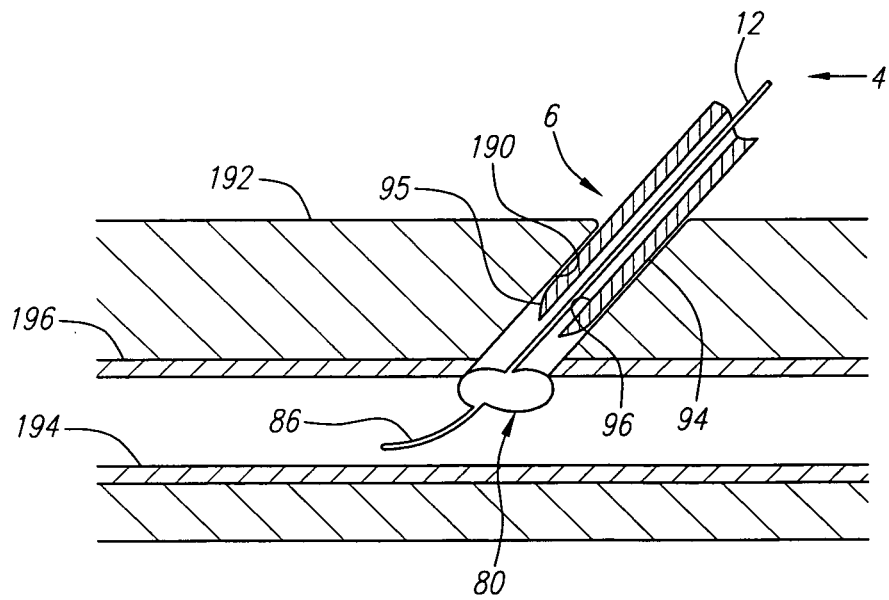

Turning to FIG. 11D (which omits the proximal components of the apparatus 2 merely for simplicity), the apparatus 2 may be partially withdrawn from the puncture 190 with the balloon 80 in the expanded state, i.e., until the balloon 80 engages the puncture 190. Preferably, the balloon 80 substantially seals the puncture 190, i.e., substantially isolating the puncture 190 from the interior of the vessel 194. Thus, the apparatus 2 may provide temporary hemostasis, e.g., preventing blood from passing through the puncture 190. Even without the additional steps that follow, the apparatus 2 may be used to provide hemostasis in emergency situations in order to minimize loss of blood until a puncture victim may be treated.

In one embodiment, the balloon 80 at least partially everts in the expanded state, as described above. This everted configuration may be particularly useful for providing hemostasis, while still allowing blood flow to continue along the vessel 194. For example, as shown in FIG. 11D, the diameter of the balloon 80 may be substantially greater than its length in the expanded state. Thus, when the balloon 80 is pulled into engagement with the wall 196 of the vessel 194, at least a portion of the vessel 194 lumen may remain unobstructed, as shown.

Figure 13:
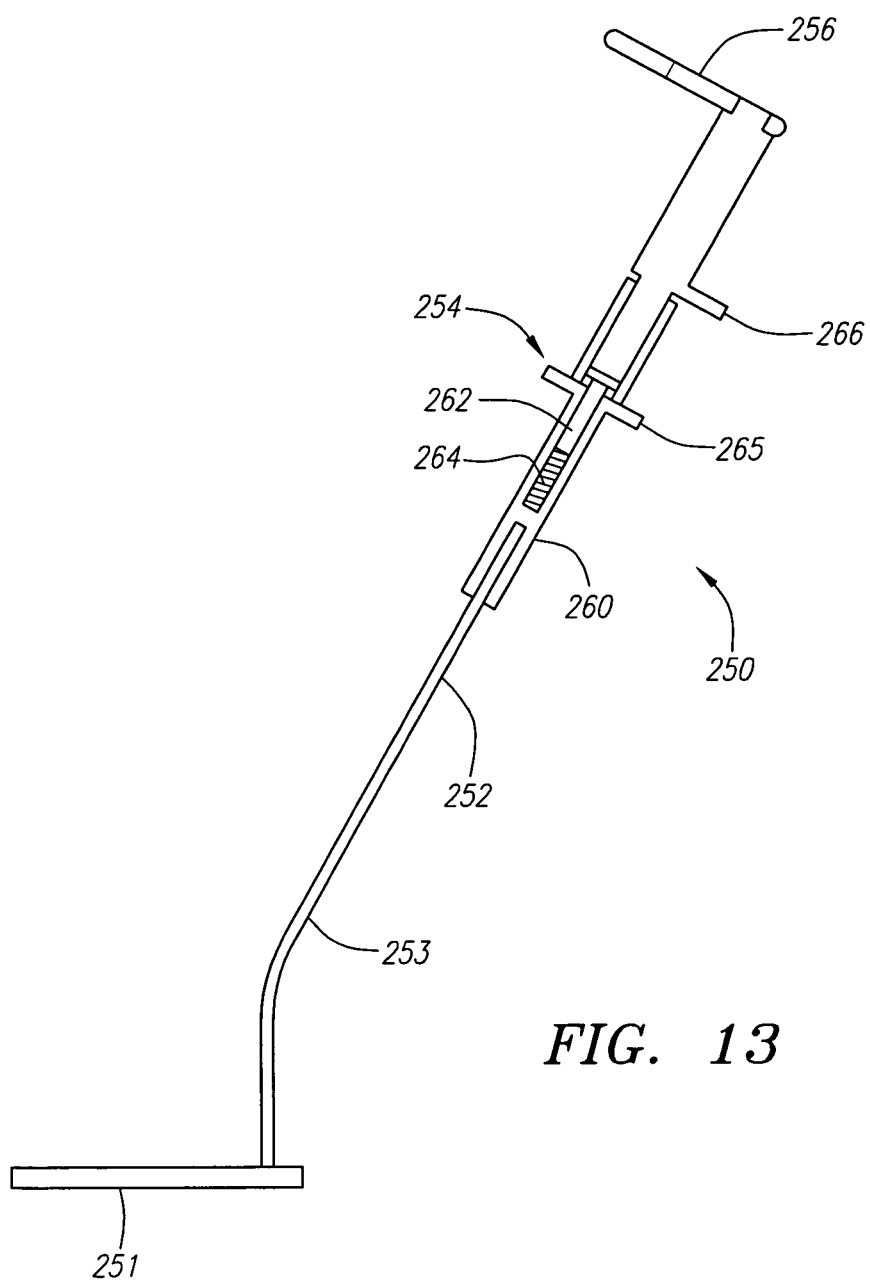
FIG. 13 is a cross-sectional view of a tensioner for supporting the occlusion member of FIGS. 12A and 12B.
Figure 14A:
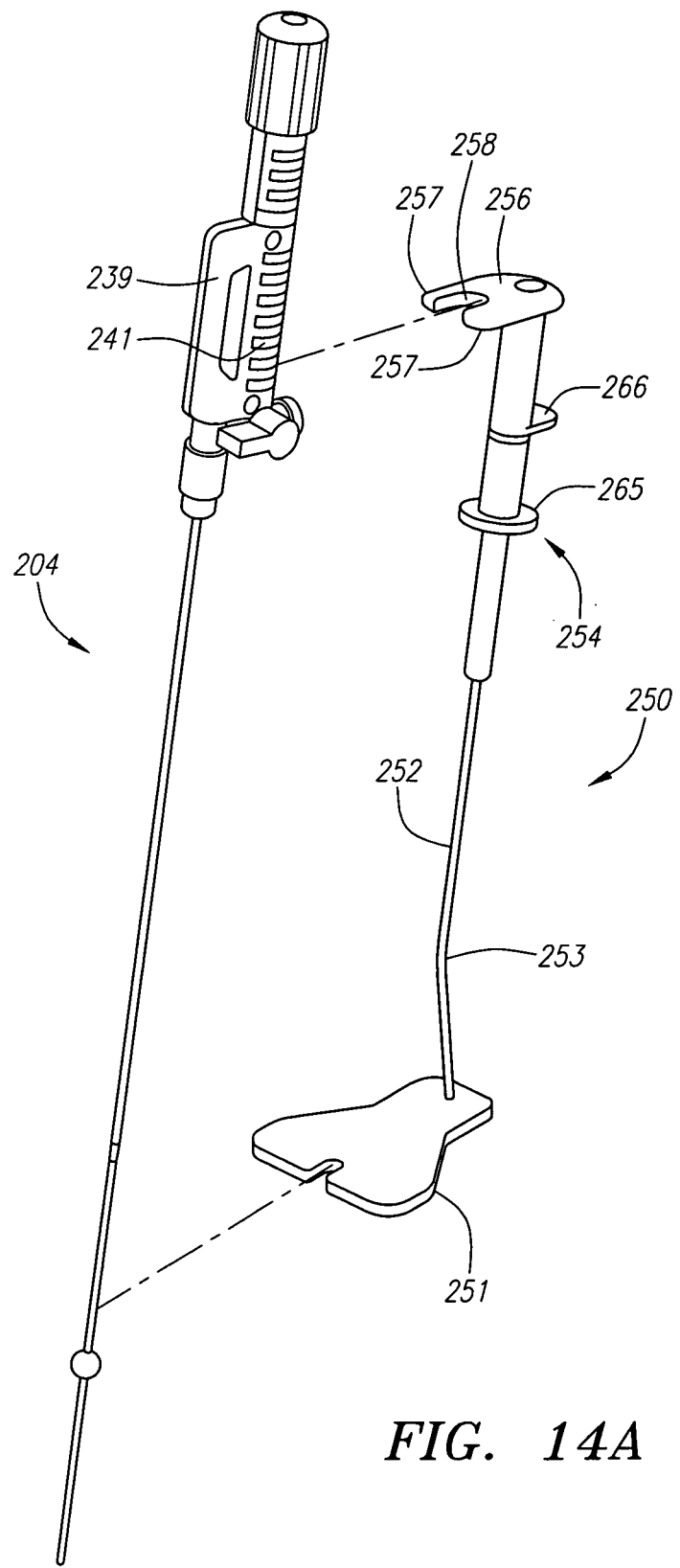
FIGS. 14A and 14B are perspective views, showing the occlusion member of FIGS. 12A and 12B being coupled to the tensioner of FIG. 13.
Figure 14B:
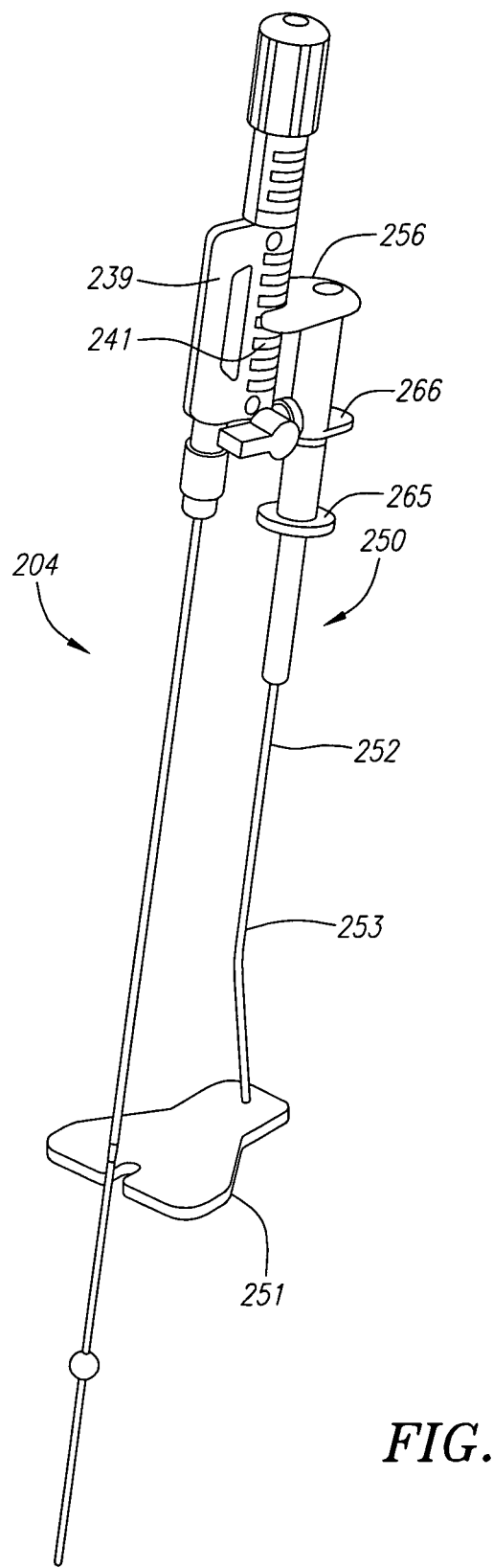

Optionally, in order to maintain the balloon 80 substantially against the puncture. 190 without requiring an individual to hold the apparatus 2, a tensioner 250 may be provided that may apply a substantially constant proximal force to the apparatus 10 to maintain the balloon 80 substantially against the puncture 190. For example, as shown in FIGS. 13, 14A, and 14B, the tensioner 250 may include a base portion or bottom foot 251, a support 252, and a saddle or top foot 256. The base portion 251 may be substantially flat or shaped to conform to the patient's anatomy, e.g., to follow the contour or otherwise lie on a patient's leg (not shown) or other skin 192 overlying the puncture 190.

The saddle 256 may include a slot 258 or other mechanism for grasping or otherwise engaging the occlusion member 204. For example, as shown in FIGS. 14A and 14B, the saddle 256 may include fingers 257 defining the slot 258. The slot 258 may have a width large enough to receive the occlusion member 204 therein, e.g., to receive a cover 239 surrounding the hub subassembly 238, while the fingers 257 are slidably received in grooves 241 in the cover 239.

The support 252 may include a substantially rigid stabilizer wire or other shaft 253, and a spring housing 254 that is slidably coupled to the saddle 256. The spring housing 254 may allow the length of the tensioner 250 to be adjustable while maintaining a substantially constant and known force on the occlusion member 204, thereby allowing the distance between the base support 251 and the saddle 256 to be adjusted based upon particular anatomy encountered during a procedure while maintaining a desired tension on the occlusion member 204.

As best seen in FIG. 13, the spring housing 254 may include a cylinder 260 extending from the stabilizer wire 253 and a piston 262 slidably received therein that extends from the saddle 256. A spring 264 or other biasing mechanism may be provided in the cylinder 260 for biasing the piston 262, and consequently, the saddle 256, away from the foot 251. Flange 266 may extend from the cylinder 260, allowing the bias of the spring 264 to be overcome by manual force, thereby causing the saddle 256 to move towards the foot 251, i.e., shortening the tensioner 250.

During use, the base portion 251 may be placed in contact with the patient, e.g., set on the patient's skin 192 adjacent to the puncture 190 (not shown, see generally, e.g., FIGS. 11A-11F). The saddle 256 may be pushed towards the foot 251 by moving flange 266 towards flange 265, e.g., until the piston 262 bottoms out in the cylinder 260. An occlusion member, such as 4 or 204, may be received in the saddle 256, e.g., by aligning the fingers 257 with a corresponding groove 241 in the cover 239. Once the occlusion member 4, 204 is engaged, the flange 266 may be released, and the bias of spring 264 may direct the saddle 256 away from the foot 251. Once the occlusion member 4, 204 resists movement of the saddle 256, i.e., matching the force from the spring 264, the tensioner 250 will stabilize and maintain the desired tension on the occlusion member 4, 204 against the wall 196 of the vessel 194.

Once the tensioner 250 is adjusted, the occlusion member 4 or 204 may be released, and the tensioner 250 may pull the occlusion member 4 or 204 10 proximally with sufficient tension to maintain the balloon 80 in contact with the wall 196 of the vessel 194. If necessary, the biasing support 252 may be adjusted to increase or decrease the distance between the saddle 256 and the base support 252 and/or to increase or decrease the tension as necessary for the anatomy encountered. Thus, the tension imposed by the tensioner 250 may apply a desired tensile force to the balloon 80 to maintain hemostasis while preventing the balloon 80 from being pulled into the puncture 190 and/or preventing the wall 196 of the vessel 194 from excessive tenting. Preferably, the spring 264 has a constant spring constant as it compresses and extends, thereby applying a constant force to the balloon 80.

It will be appreciated that other configurations may be provided for the tensioner 250 than that shown in FIGS. 13-14B. For example, the saddle may be slidable along the shaft connected to the foot, and a constant force spring, e.g., a coil spring, extension spring, compression spring, and the like, may be coupled between the saddle and the shaft to bias the saddle away from the foot or otherwise as desired. Alternatively, the spring may provided a variable force along the movement range of the saddle, e.g., providing greater or lesser resistance as the saddle is directed towards the foot.

Figure 11E:
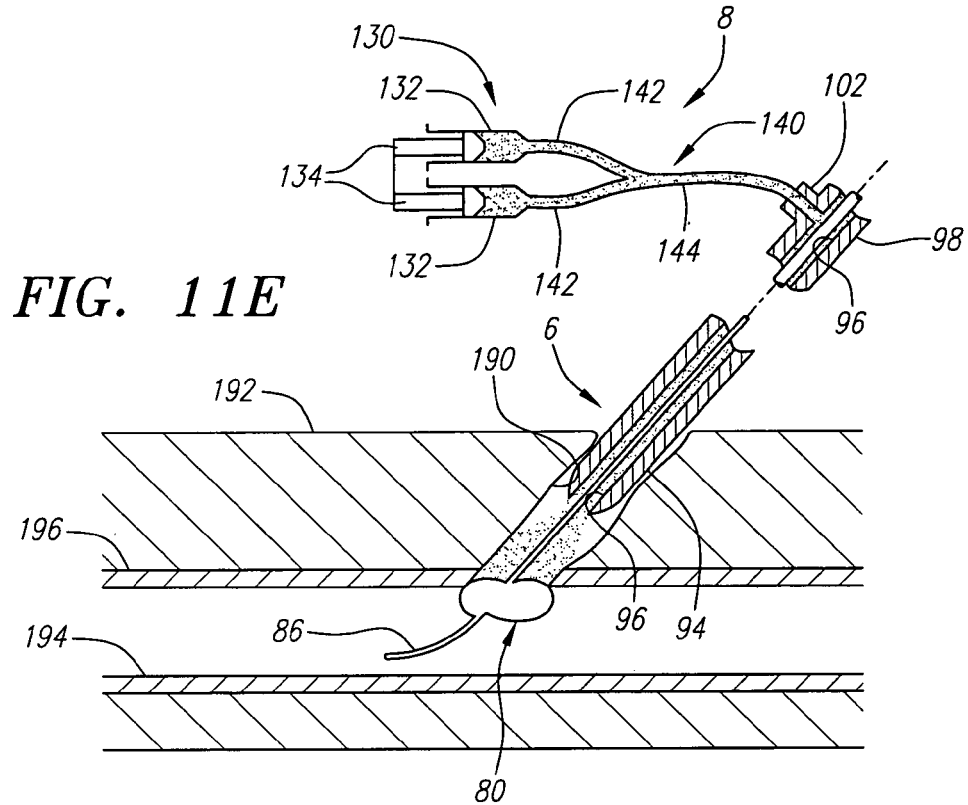

Turning to FIG. 11E, once the occlusion member 4 is adjusted to seal the puncture 190 from the vessel 194, a sealing compound 146 may be delivered into the puncture 190. Preferably, the sealing compound is a liquid or other flowable material that may be injected into the puncture 190. Because of the hemostasis provided by the balloon 80, the sealing compound 146 may be delivered without substantial concern that the sealing compound 146 may leak into the vessel 194. As explained above, relative movement of the introducer sheath 90 and the occlusion member 4 may be limited to maintain a minimum distance between the distal end 96 of the introducer sheath 90 and the balloon 80. This may reduce the risk of sealing material being injected into the vessel 194.

The sealing compound may include multiple precursor polymer components that create a hydrogel when mixed together, as described above. Such a sealing compound may be particularly useful, because it may be substantially harmless to the patient even if it somehow leaks into the vessel 194. Unlike collagen or other hemostasis-promoting materials, which may cause thrombosis and/or embolism when exposed to blood within a vessel, hydrogel polymers may not promote hemostasis within a blood vessel. In fact, such hydrogels, if leaked into a vessel, may simply dilute and flow away, where they may be metabolized naturally without substantial risk of creating thrombus. This is another reason why it may be useful to seal the puncture 190 with an everted balloon 80, while still allowing fluid to continue to flow along the vessel 194, as described above. In case the hydrogel leaks into the vessel 194 around the balloon 80, blood flow may dilute and carry the hydrogel away, where it may be safely metabolized naturally.

As shown in FIG. 11E, a two-part sealing compound is shown contained within the dual syringe assembly 130. The precursor polymers or other components in the syringe barrels 132 may be mixed or otherwise prepared before the procedure using known methods. The plunger assembly 133 may be manually depressed, thereby advancing the plungers 134 substantially simultaneously, and delivering the precursor polymer compounds simultaneously. The precursor polymers may mix in the "Y" fitting 140 into a liquid sealing compound 146, and then be delivered into the side port 102 of the introducer sheath 90 via the mixer 110 and tubing 106. Alternatively, an auto-injector device (not shown) may be provided for delivering the precursor polymers at a desired substantially continuous rate, as described further below.

Figure 11F:
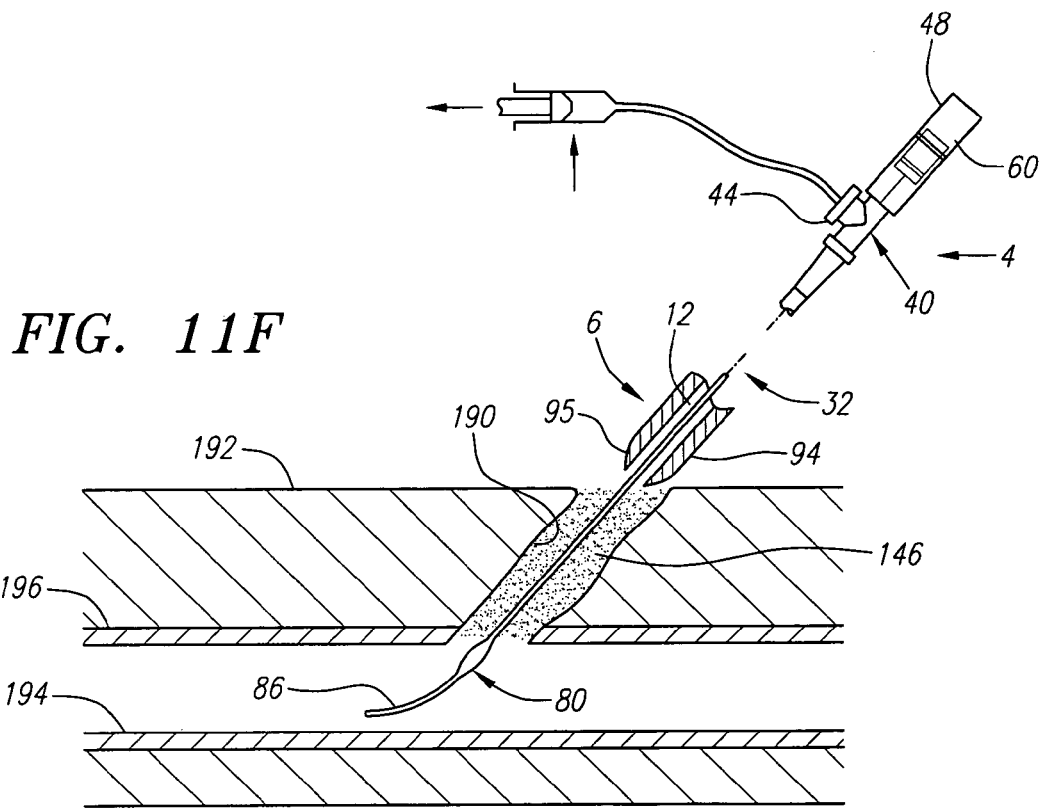

The liquid sealing compound 146 may be injected through the lumen 96 of the introducer sheath 90 out the distal end 94 into the puncture 190. As the plunger assembly 133 is depressed, the piston 135 may slidably engage the release button 126, e.g., bearing against the sloped proximal surface 126a (not shown, see FIGS. 10A and 10B). This causes the lock member 124 to move inwardly, thereby releasing the shaft 114, as described above. Once the shaft 114 is released, the spring 122 may cause the shaft 114 to move proximally. This may cause the introducer sheath 90 to be withdrawn proximally from the puncture 190 as the sealing compound 146 is delivered, thereby filling the puncture tract with the sealing compound 146, as shown in FIG. 11F. Proximal movement of the shaft 114 is preferably limited, e.g., to prevent the introducer sheath 90 from being withdrawn completely from the puncture 190 as the sealing compound 146 is delivered.

It will be appreciated that other devices may be used for delivering sealing material into the puncture 190. For example, other apparatus for delivering liquid sealing compounds, including single or multiple lumens (not shown), may be advanced over the occlusion member 4 instead of the single lumen introducer sheath 90.

Turning to FIG. 11F, once the sealing compound 146 is delivered, the sealing compound 146 may be given sufficient time to at least partially (or fully) solidify or gel, e.g., between about five and one hundred eighty (5-180) seconds. The balloon 80 may then be deflated to the collapsed state and then withdrawn from the puncture 190. As described above, the balloon 80 may preferably be extended distally as it collapses to facilitate its removal through the sealing compound 146 delivered into the puncture 190. Optionally, to facilitate removing the occlusion member 4, a lubricious coating (not shown) may be provided on the exterior of the outer member 12, sheath 530 (not shown, see FIG. 18A), and/or balloon 80, e.g., Dow 360 silicone fluid. Such a coating may prevent the sealing compound 146 from sticking to or otherwise pulling on the occlusion member 4 as it is withdrawn.

Optionally, external pressure may be applied, e.g., by pressing manually against the skin 192 overlying the vessel 194, e.g., to at least partially suppress flow through the vessel 194. The balloon 80 (and the rest of the apparatus 10) may be removed, and the external pressure may be maintained for sufficient time to allow the sealing compound 146 to solidify further, e.g., between about ten and one hundred eighty (10-180) seconds. The sealing compound may expand, e.g., due to its elasticity and/or due to further solidification, thereby substantially sealing the relatively small tract remaining upon removing the apparatus 10.

Alternatively, the tensioner 150 (not shown, see FIGS. 13A-14B) may be used to maintain tension on the balloon 80 for a prolonged period of time with the balloon 80 providing temporary hemostasis to allow the hydrogel to cure fully in the puncture 190 before removing the apparatus 10.

Figure 19A:
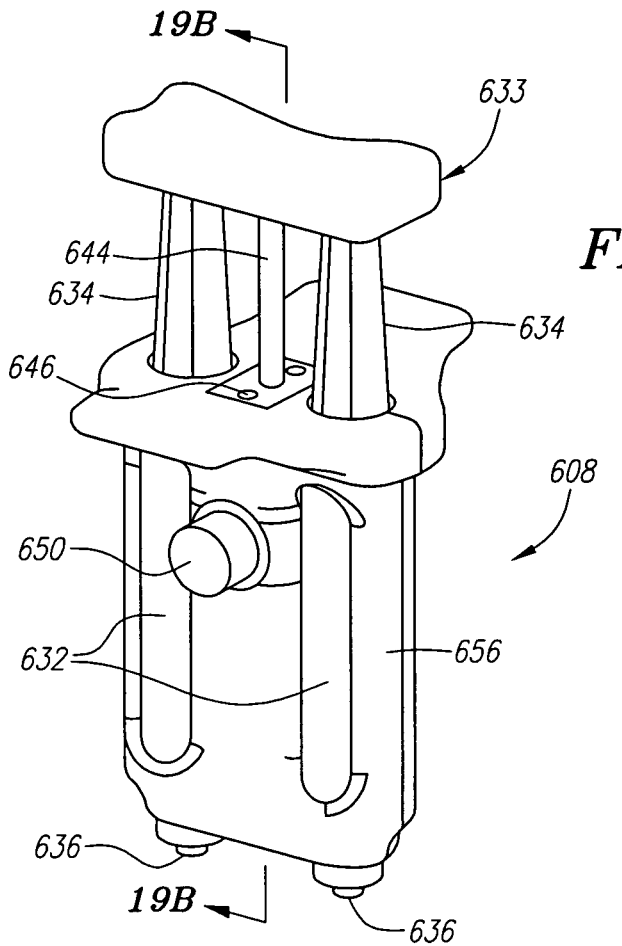
FIG. 19A is a perspective view of an auto-injector device for delivering a sealing compound.
Figure 19B:
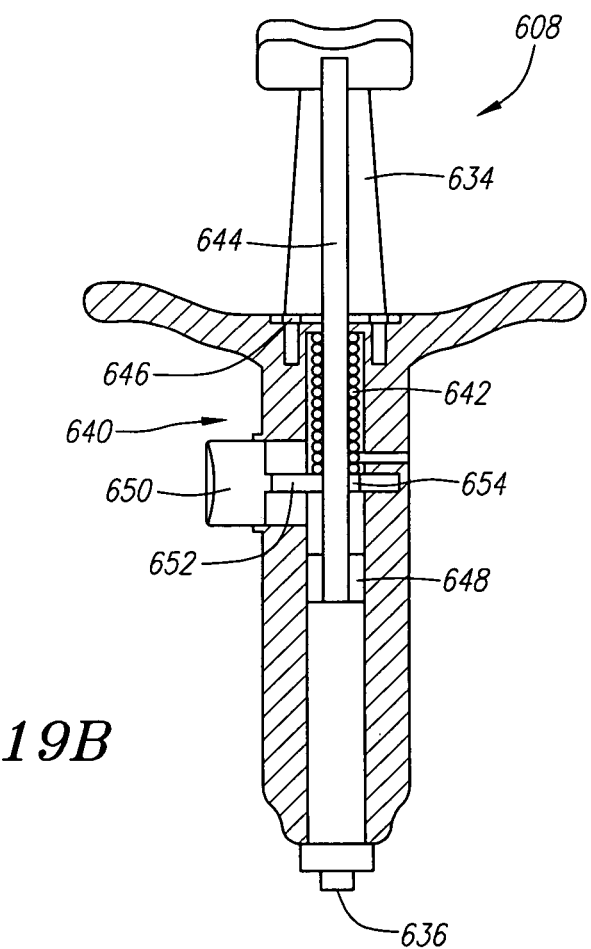
FIG. 19B is a cross-section of the auto-injector device of FIG. 19A, taken along line 19B-19B.
Figure 19C:
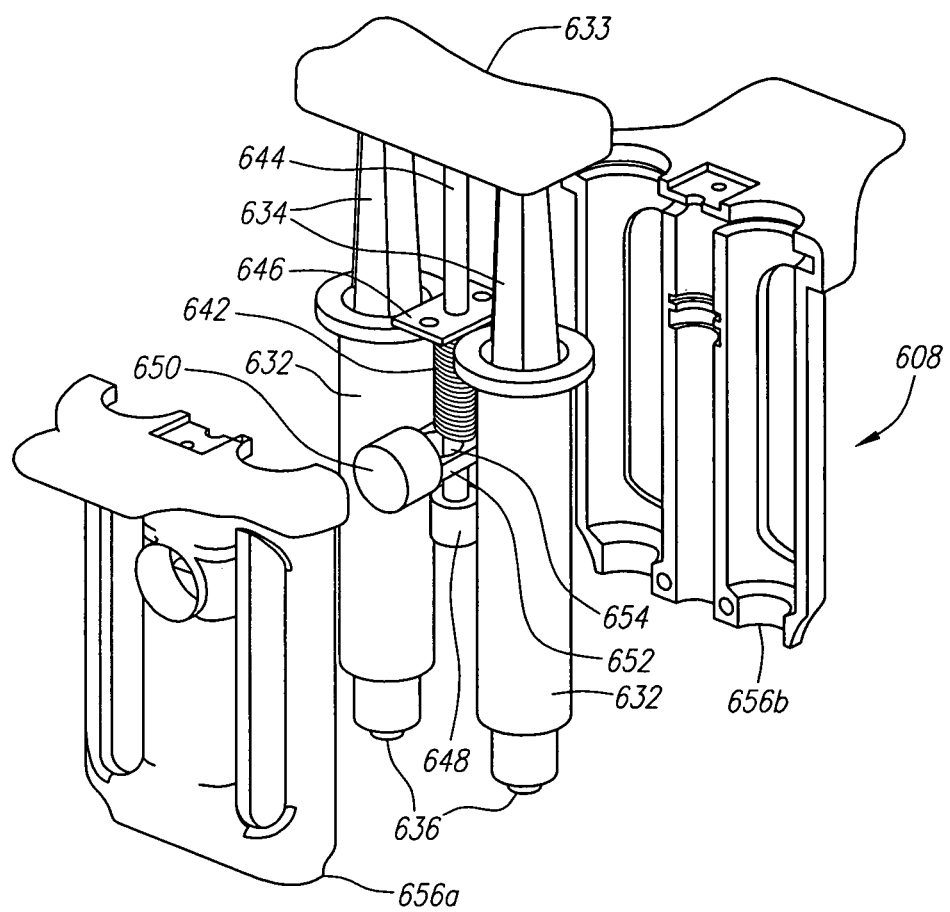
FIG. 19C is an exploded perspective view of the auto-injector device of FIG. 19A.

Turning to FIGS. 19A-19C, an exemplary embodiment of a delivery device 608 for automatically delivering sealing compound is shown that may be provided instead of a manually injected system, such as those described above. In the embodiment shown, the delivery device 608 (which may also be referred to as an auto-injector assembly) includes a pair of syringe barrels 632 including outlets 636 and defining a longitudinal axis 620. It will be appreciated that the delivery device 608 may include one or more syringe barrels, depending upon the type of sealing compound being delivered.

A plunger assembly 133 is slidable axially relative to the barrels 636. In one embodiment, the plunger assembly 633 includes a pair of plungers 634 that are coupled to one another yet are received in respective barrels 632. Thus, both plungers 134 may be advanced into or retracted from the barrels 632 substantially simultaneously with one another.

The delivery device 608 also includes a spring mechanism 640 (best seen in FIG. 19B) that may be activated to cause the plunger assembly 633 to advance automatically into the barrels 632. As shown, the spring mechanism 640 includes a spring 642 disposed around a shaft 644 extending from the plunger assembly 633. The spring 642 is disposed adjacent to a hub or barrel plate 646 extending between the barrels 632, thereby fixing a first or upper end of the spring 642 relative to the barrels 632. The shaft 644 extends distally from the plunger assembly 633 between the barrels 632, and terminates in an enlarged head 648. Preferably, the head 648 is larger than the diameter of the spring 642 and/or includes one or more radial elements (not shown) against which the spring 642 may push when released.

The spring mechanism includes an actuation button 650 that may be coupled to an interference plate 652 that extends transversely relative to the longitudinal axis 620 such that the spring 642 is disposed between the plate 646 and the interference plate 652. In the embodiment shown, the actuation button 650 and interference plate 646 are integrally molded or otherwise formed as a single piece, although alternatively, they may be separate pieces attached to one another.

In one embodiment, the spring 642 is a compression spring that is compressed when disposed initially between the plate 646 and the interference plate 652. The actuation button 650 and interference plate 652 are movable from a first locked or outer position, and a second release or inner position.

The interference plate 652 includes a passage 654 extending axially therethrough that has cross-section larger than the diameter of the spring 652. In the first position, the passage 654 is offset from the spring 652, such that a second or lower end of the spring 652 bears against the interference plate 652. When the actuation button 650 is directed to the second position, the passage 654 becomes aligned with the spring 652. This action releases the spring 652, allowing the spring to pass through the passage 654 and push against the head 648, thereby directing the head 648, and consequently the shaft 644, distally relative to the barrels 632. As the shaft 644 moves distally, the plunger assembly 633 is advanced into the barrels 632 to inject the sealing compounds out of the barrels 632 through the outlets 636.

Optionally, the delivery device 608 may include a cover or casing 656 that may at least partially enclose the spring mechanism 640 and/or the barrels 632. In addition, the delivery device 608 may include a valve, tubing, containers storing sealing components, a "Y" fitting, and/or a mixer, similar to the embodiments described above. For example, FIGS. 16A and 16B show an embodiment of a delivery device 308, including a spring mechanism 340 similar to that described above.

With reference to the delivery device 308 shown in FIGS. 16A and 16B, during use, sealing components may be provided in the barrels 332 with the plunger assembly 333 in a first proximal position. For example, initially, one or more solvents, buffer solutions, and/or other sealing components may be provided in the syringe barrels 332, e.g., filled during manufacturing. Vials 320 may be provided that include additional sealing components that may be mixed or reconstituted with the sealing components in the barrels 332.

Shortly before delivering the sealing components, the valve 310 may be moved to a first position wherein the outlets 336 of the barrels 332 communicate with the vials 322. The plunger assembly 333 may be manually advanced into the barrels 332 to inject the sealing components in the barrels 332 into the vials 322. In one embodiment, the solvents or buffer solutions in the barrels 332 are injected into the vials 322 that include solid polymer precursor components, for example, in powder or other solid form, to reconstitute or otherwise mix the precursor polymer components.

Once the buffer solution is injected into the vials 322, the vials 322 may be shaken, e.g., by shaking the entire delivery device 308, to dissolve the polymer precursor components in the one or more buffer solutions. Once the sealing components are mixed and/or reconstituted, the plunger assembly 333 may be manually withdrawn at least partially from the barrels 332 to draw the mixed sealing components from the vials 322 into the barrels 332. Preferably, the plunger assembly 333 is withdrawn a predetermined distance to a load a desired volume into the barrels 332 based upon the volume of the puncture to be sealed.

Once the reconstituted/mixed sealing components are loaded in the barrels 332, the valve 320 may be moved to a closed position, and the delivery device 308 may be set aside, e.g., while one or more medical procedures may be performed on the patient. Upon completing the procedure(s), the valve 320 may be moved to a delivery position, wherein the outlets 336 communicate with the "Y" fitting 339 and delivery line (not shown) that communicates with a delivery sheath (also not shown), such as any of the devices described elsewhere herein.

At the time of delivery, the actuation button 350 may be activated to release the spring 342, which may then push on the shaft 344, thereby advancing the plunger assembly 333 into the barrels 332, and injecting the sealing components out of the barrels 332. One advantage of an auto-injector delivery device, such as those described herein, may prevent unintended pauses during delivery. Such interruptions risk occluding the delivery line, i.e., the "Y" fitting, mixer, or other passages through which the sealing compound passes. This may be a particular concern where the sealing compound has a relatively short gel or set-up time. The spring constant of the spring mechanism may be predetermined to ensure that the sealing compound is delivered in a desired time, i.e., before the sealing compound gels and ceases to flow through the delivery line.

Turning to FIGS. 20A-20F, another embodiment of an auto-injector assembly 708 is shown. Similar to the previous embodiment, the assembly 708 includes a pair of syringe barrels 732 including outlets 736 and a plunger assembly 733 slidable relative to the barrels 732. The plunger assembly 733 includes a pair of plungers 734 slidably disposed in the barrels 732, and a pair of pistons 735 slidable within the barrels 732 relative to the plungers 734. Springs 637 are also provided within the barrels 732 that are coupled between the plungers 734 and the pistons 735. It will be appreciated that the barrels 732, plungers 734, and/or pistons 735 may include one or more connectors, e.g., detents, stops, and the like (not shown) that limit relative movement of the parts relative to one another and/or prevent the assembly 708 from coming apart during use.

The springs 737 may have a predetermined spring constant such that the plungers 734 and pistons 735 may be directed towards one another, when axial forces are applied. When the forces are removed, the springs 737 bias the plungers 734 and pistons 735 to move away from one another to return to the springs 737 a relaxed state.

The plungers 734 and/or the barrels 732 may include cooperating connectors or other locking elements (not shown) that may be selectively activated to secure the plungers 734 relative to the barrels 732, e.g., to lock the plungers 734 in a depressed position where the plungers 734 are advanced into the barrels 732. The locking elements may include cooperating detents, ratchets, latches, and the like (not shown), as is known in the art.

In one embodiment, shut-off valves (not shown) may be provided in the outlets 736 to selectively open and close the outlets 736. Alternatively, a multiple port valve, such as those shown in FIGS. 15 and 17A-17C, may be provided that eliminate the need to change connections to the outlets 736 during a procedure.

Figure 20A:
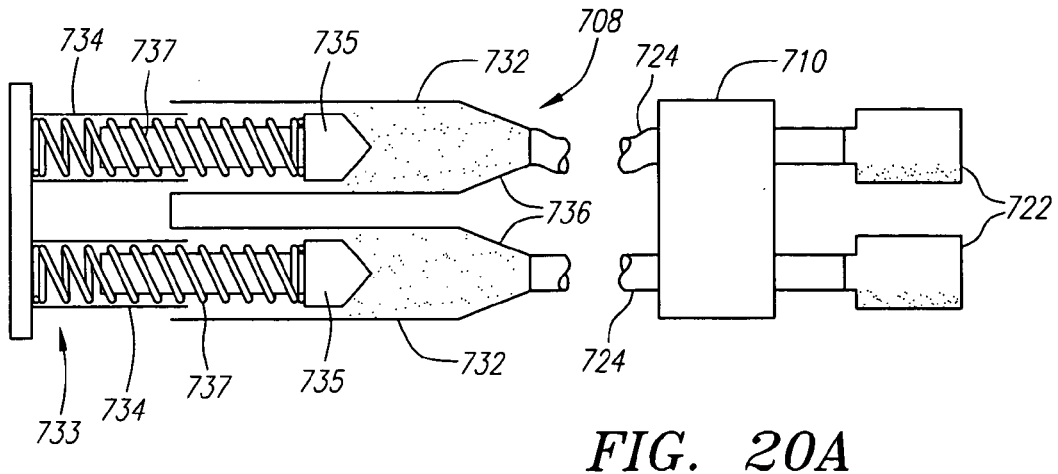
FIGS. 20A-20F are cross-sectional views of another embodiment of an auto-injector device, including internal springs.

Initially, before use, the assembly 708 is provided with sealing components in the barrels 708, e.g., one or more solvents or buffer solutions, as shown in FIG. 20A. The barrels 708 may include a predetermined volume intended to be mixed with powdered or other solid polymer precursor components, e.g., provided in vials 322, similar to the previous embodiments. With the barrels 708 filled with the sealing components, the pistons 735 and plungers 735 may be retracted from the barrels 708 such that the springs 737 are substantially relaxed. Alternatively, if the springs 737 are not fully relaxed, the valve 710 may be closed to prevent the sealing components from being injected out of the barrels 708 by the potential of the springs 737.

Shortly before use of the assembly 708, e.g., while preparing for a medical procedure involving creation of a puncture through tissue that is to be sealed, the valve 710 may be positioned such that the outlets 736 communicate with the vials 722. In one embodiment, the vials 722 may be provided already attached to the assembly 708, similar to the embodiment shown in FIGS. 16A and 16B. Alternatively, the vials 722 may be attached to the valve 710 or even directly to the outlets 736.

Figure 20B:
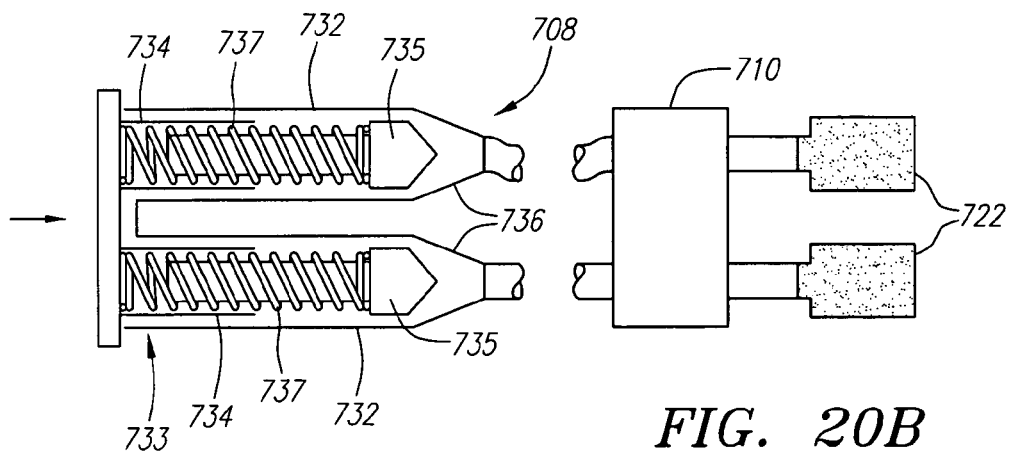
Figure 20C:
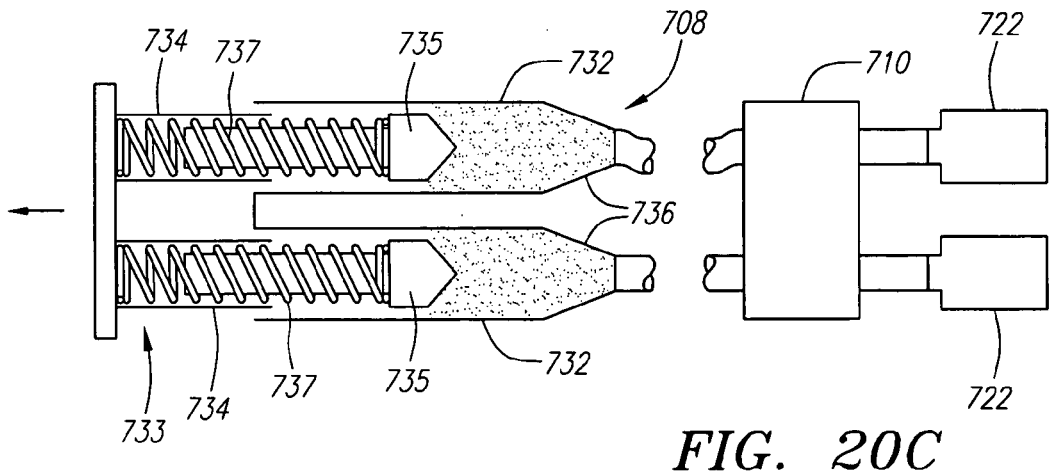

As shown in FIG. 20B, the sealing components in the barrels 732 may be injected into the vials 722 by depressing the plunger assembly 733, advancing the pistons 735 distally. The sealing components may be mixed and/or reconstituted in the vials 722, similar to the previous embodiments. Once mixed, the plunger assembly 733 may be retracted to draw a desired volume of the mixed sealing components into the barrels 732, as shown in FIG>20C.

Figure 20D:
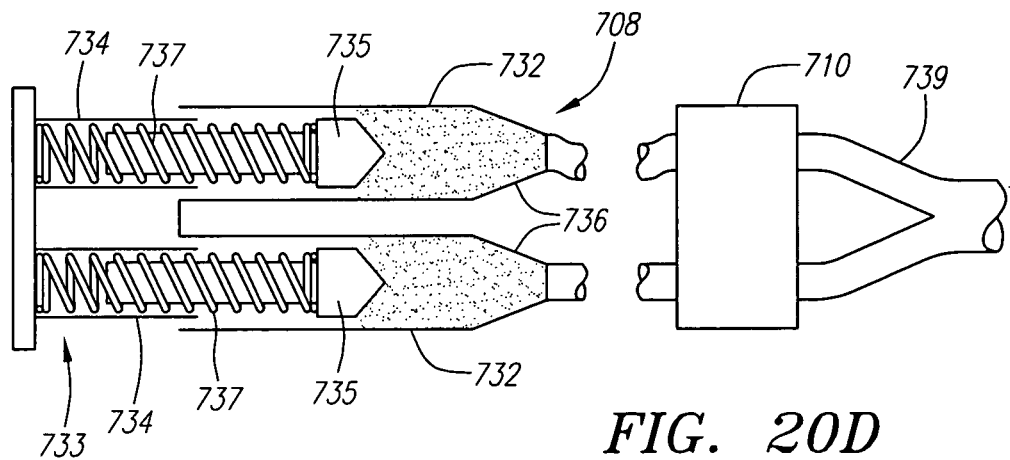

The assembly 708 is then prepared, and the valve 710 may be closed to store the sealing components during the procedure. If the valve 710 is a multiple port valve, a delivery line, e.g., including "Y" fitting 739 may already be connected to the valve 710, similar to the embodiment shown in FIGS. 16A and 16B. If the valve 710 is simply a shut-off valve, the vials 722 may be disconnected, and the "Y" fitting 739 and/or other delivery line may be connected to the valve 710, as shown in FIG. 20D.

Figure 20E:
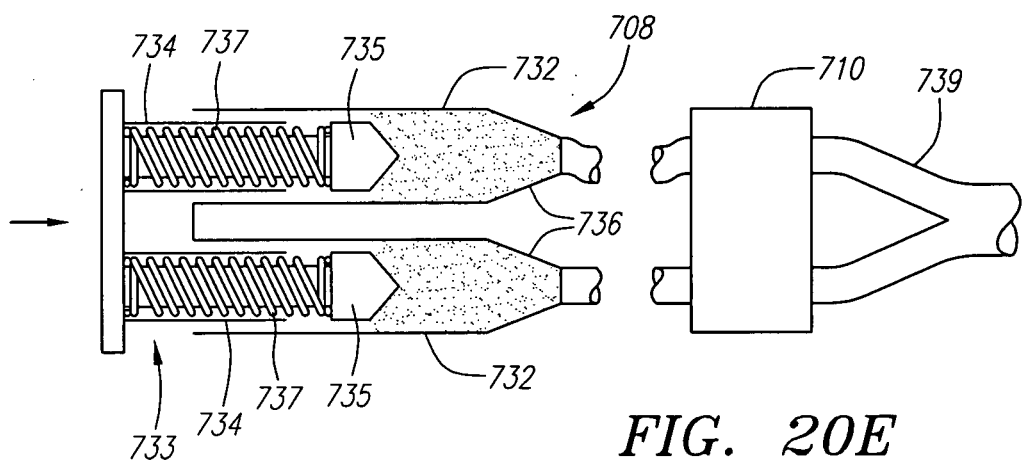

At any time, e.g., when it is time to deliver the sealing components in the barrels 732, the plunger assembly 733 may be depressed while the valve 710 remains closed, causing the plungers 734 to advance into the barrels 732. Because the valve 710 is closed, the pistons 735 are unable to move substantially, thereby causing the springs 737 to compress, as shown in FIG. 20E. Once the plunger assembly 733 is depressed to a desired position, the plunger assembly 733 may be locked to prevent the springs 737 from pushing the plunger assembly 733 back out of the barrels 732. This may involve closing a latch or other connector (not shown). Alternatively, the plunger assembly 733 may include cooperating ratchets (also not shown), e.g., on the plungers 734, that may allow the plungers 734 to advance into but not retract out of the barrels 732.

With the plunger assembly 733 locked in the advanced position shown in FIG. 20E, the springs 737 are under compression, and are therefore biased to direct the pistons 735 distally into the barrels 732. When the delivery line is established, e.g., including an introducer sheath, delivery sheath, and the like disposed within the puncture to be sealed (not shown), the valve 710 may be opened or moved to the delivery position such that the outlets 736 communicate with the "Y" fitting 739 and/or delivery line.

Figure 20F:
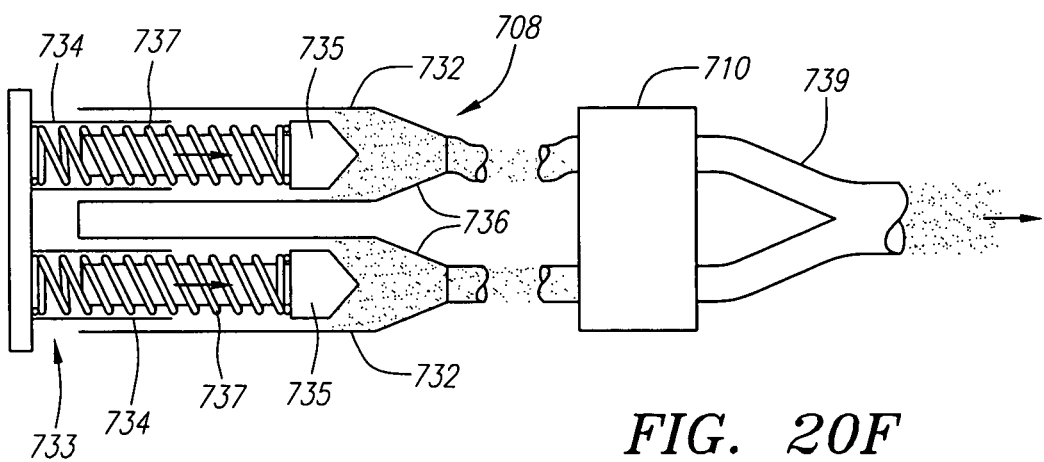

As shown in FIG. 20F, the bias of the springs 737 push the pistons 735 distally to inject the sealing components out of the barrels 732 through the outlets 736. The sealing components may then mix and/or otherwise travel through the delivery line into the puncture, similar to the embodiments described above.

One advantage of the internal spring arrangement of the embodiment of FIGS. 20A-20F is that a cover may not be needed, because the springs are located within the barrels. In contrast, the external spring arrangement of FIGS. 19A-19C, because the spring 642 is outside the barrels 632, a cover 656 may be desired to conceal and protect the spring 642 from damage.

The foregoing detailed description includes passages that are chiefly or exclusively concerned with particular features or aspects of particular embodiments of the invention. It should be understood that this is for clarity and convenience, and that a particular feature may be relevant in more than just the passage in which it is disclosed and embodiment in which it is described. Similarly, although the various figures and descriptions herein relate to specific embodiments of the invention, it is to be understood that where a specific feature is disclosed in the context of a particular figure or embodiment, such feature may also be used, to the extent appropriate, in the context of another figure or embodiment, in combination with another feature, or in the invention in general.

For example, while various embodiments of retraction assemblies, auto-injector assemblies, occlusion members, and the like have been described herein in exemplary combinations with one another, it will be appreciated by those skilled in the art that the described embodiments may be interchanged with one another without departing from the scope of the invention.

Further, it should be understood, that the invention is not to be limited to the particular described embodiments, but is to cover all modifications, equivalents and alternatives falling within the scope of the appended claims.

It will be appreciated that many embodiments of retraction assemblies, auto-injector assemblies, occlusion members, and the like have been described herein in exemplary combinations with one another. It will be appreciated by those skilled in the art that the various embodiments may be interchanged with one another without deviating from the scope of the present invention.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

What is claimed:

1. An apparatus for sealing a puncture extending through tissue, comprising:
    a tubular member having a proximal end, a distal end sized for insertion into the puncture, and a lumen extending between the proximal end and an outlet at the distal end;
    an elongate occlusion member slidably disposed within the tubular member, the occlusion member comprising a proximal end, and a distal end extending distally through an opening in the distal end of the tubular member;
    an expandable member on the occlusion member distal end;
    a delivery device coupled to the proximal end of the tubular member, the delivery device comprising a plunger that is advanceable to deliver a sealing compound from the tubular member lumen around the occlusion member and from the outlet at the distal end of the tubular member; and
    a retraction assembly coupled to the proximal end of the tubular member and to the occlusion member, the retraction assembly comprising a lock for securing the tubular member in a distal position relative to the occlusion member, and a trigger that is activated by advancement of the plunger to thereby disengage the lock, the retraction assembly being biased to retract the tubular member proximally relative to the occlusion member when the lock is disengaged such that the tubular member is retracted and the occlusion member remains substantially stationary while delivering the sealing compound from the tubular member lumen out the outlet at the distal end of the tubular member.

2. The apparatus of claim 1, the occlusion member further comprising:
    an outer member comprising proximal and distal ends defining a longitudinal axis therebetween with an inflation lumen extending between the outer member proximal and distal ends, the expandable member comprising proximal and distal ends and having a variable length dimension, the proximal end of the expandable member being coupled to the distal end of the outer member such that an interior of the expandable member is in fluid communication with the inflation lumen, the expandable member being expandable from a collapsed state to an expanded state by introduction of fluid into the interior; and
    an inner member slidably coupled to the outer member and comprising proximal and distal ends, the inner member distal end coupled to the expandable member distal end, the inner member slidable relative to the outer member for moving the distal end of the expandable member towards and away from the proximal end of the expandable member when the expandable member is expanded and collapsed, respectively.

3. The apparatus of claim 2, further comprising a housing on the proximal end of the outer member, the housing comprising a chamber in fluid communication with the inflation lumen, a piston slidably disposed within the chamber and coupled to the inner member, a reservoir filled with inflation media and in fluid communication with the chamber, and an actuator that may be activated by a user to direct the inflation media from the reservoir into the chamber and inflation lumen, thereby substantially simultaneously expanding the expandable member and directing the piston proximally to thereby pull the inner member proximally to shorten the expandable member as it expands.

4. The apparatus of claim 3, wherein the actuator may be deactivated to withdraw inflation media from the chamber and the inflation lumen into the reservoir, thereby substantially simultaneously collapsing the expandable member and directing the piston distally to push the inner member distally to lengthen the expandable member as it collapses.

5. The apparatus of claim 3, wherein the proximal and distal ends of the expandable member at least partially evert into the interior of the expandable member as the expandable member expands.

6. The apparatus of claim 1, the retraction assembly further comprising an elongate member extending distally along a proximal portion of the occlusion member, the elongate member comprising one or more connectors on a distal end thereof, the one or more connectors connectable to the proximal end of the tubular member to thereby couple the tubular member to the retraction assembly.

7. The apparatus of claim 6, wherein the occlusion member is coupled to the retraction assembly, the elongate member further comprising a sheath extending over the proximal portion of the occlusion member, wherein the sheath may be received in the tubular member lumen when the occlusion member is inserted therein, the one or more connectors being insertable at least partially into the proximal end of the tubular member to couple the tubular member to the sheath.

8. The apparatus of claim 7, the tubular member further comprising a housing on the proximal end thereof, the housing defining a cavity, the one or more connectors comprising a detent that collapses to allow the detent to be inserted into the cavity when the sheath is received in the tubular member lumen, the detent being biased to extend within the cavity and prevent the detent from being removed easily therefrom.

9. The apparatus of claim 8, the housing comprising one or more side ports communicating with the delivery device, the sheath comprising a lumen and an opening communicating with the lumen that is disposed within the cavity when the detent is inserted into the cavity, the sheath comprising a seal distal to the opening for engaging an inner surface of the tubular member to substantially seal the lumen of the tubular member, such that sealing compound delivered from the delivery device enters the one or more side ports and flows into the opening and through the lumen of the sheath.

10. The apparatus of claim 9, wherein a distal tip of the sheath extends beyond the distal end of the tubular member when the detent is inserted into the cavity, such that the sealing compound is delivered through the lumen of the sheath out the distal tip of the sheath and beyond the distal end of the tubular member.

11. The apparatus of claim 1, wherein the lock is configured to be disengaged while delivering the sealing compound out the distal end of the tubular member.

12. The apparatus of claim 1, wherein the delivery device is coupled to a side port on the proximal end of the tubular member for delivering the sealing compound through the tubular member lumen.

13. An apparatus for sealing a puncture extending through tissue, comprising:
    an outer member comprising proximal and distal ends defining a longitudinal axis therebetween with an inflation lumen extending between the outer member proximal and distal ends;
    an expandable member comprising proximal and distal ends and having a variable length dimension, the proximal end of the expandable member being coupled to the distal end of the outer member such that an interior of the expandable member is in fluid communication with the inflation lumen, the expandable member being expandable from a collapsed state to an expanded state by introduction of fluid into the interior;
    an inner member slidably coupled to the outer member and comprising proximal and distal ends, the inner member distal end coupled to the expandable member distal end, the inner member slidable relative to the outer member for moving the distal end of the expandable member towards and away from the proximal end of the expandable member when the expandable member is expanded and collapsed, respectively;
    a housing on the proximal end of the outer member, the housing comprising a chamber in fluid communication with the inflation lumen, a piston slidably disposed within the chamber and coupled to the inner member, a reservoir having a cross-section larger than the inflation lumen filled with inflation media and in fluid communication with the chamber via a passage, and an actuator that may be activated by a user to direct the inflation media from the reservoir into the chamber and inflation lumen, the inflation media substantially thereby simultaneously expanding the expandable member and directing the piston proximally to thereby pull the inner member proximally to shorten the expandable member as it expands;
    a tubular member having a proximal end, a distal end sized for insertion into the puncture, and a lumen extending between the proximal and distal ends, the outer member being slidable through the tubular member;
    a delivery device coupled to the proximal end of the tubular member, the delivery device comprising a plunger that is advanceable to deliver a sealing compound from the tubular member lumen into the puncture; and
    a retraction assembly coupled to the proximal end of the tubular member and to the housing, the retraction assembly comprising a lock for securing the tubular member in a distal position relative to the expandable member, and a trigger that is activated by advancement of the plunger to thereby disengage the lock, the retraction assembly being biased to retract the tubular member proximally relative to the expandable member when the lock is disengaged.

14. An apparatus for sealing a puncture extending through tissue, comprising:
    a tubular member having a proximal end, a distal end sized for insertion into the puncture, and a lumen extending between the proximal end and an outlet at the distal end;
    an elongate occlusion member slidably disposed within the tubular member, the occlusion member comprising a proximal end, and a distal end extending distally through an opening in the distal end of the tubular member;
    an expandable member on the occlusion member distal end;
    a delivery device for delivering a sealing compound from the tubular member lumen around the occlusion member and from the outlet at the distal end of the tubular member; and
    a retraction assembly coupled to the proximal end of the tubular member and to the occlusion member, the retraction assembly comprising a lock for securing the tubular member in a distal position relative to the occlusion member, and a trigger that is activatable to disengage the lock, the retraction assembly being biased to automatically retract the tubular member proximally relative to the occlusion member when the lock is disengaged such that the tubular member is retracted and the occlusion member remains substantially stationary while delivering the sealing compound from the tubular member lumen out the outlet at the distal end of the tubular member to at least partially fill the puncture.

15. The apparatus of claim 14, wherein the retraction assembly comprises a stop that limits proximal retraction of the tubular member relative to the occlusion member when the lock is disengaged.

16. The apparatus of claim 15, wherein the stop is disposed at a location such that proximal retraction of the tubular member corresponds substantially to a length of a puncture through tissue that is being sealed.

17. The apparatus of claim 14, wherein the delivery device comprises a plunger that is advanceable to deliver the sealing compound through the tubular member lumen and out the distal end of the tubular member, and wherein the trigger is activated by advancement of the plunger to thereby disengage the lock.

18. The apparatus of claim 17, wherein the trigger and lock are spaced apart a predetermined distance such that the lock is released when the sealing compound begins to exit from the distal end of the tubular member.

* * * * *